(12) United States Patent
Rufty

(10) Patent No.: US 6,965,062 B2
(45) Date of Patent: Nov. 15, 2005

(54) TOBACCO CULTIVAR NC 2000

(75) Inventor: Rebeca C. Rufty, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/247,857

(22) Filed: Sep. 20, 2002

(65) Prior Publication Data

US 2003/0115642 A1 Jun. 19, 2003

Related U.S. Application Data

(60) Provisional application No. 60/323,908, filed on Sep. 21, 2001.

(51) Int. Cl.$^7$ .............................. A01H 5/00; A01H 5/10; A01H 1/00; C12N 15/82; C12N 5/04
(52) U.S. Cl. .................... 800/317.3; 800/260; 800/265; 800/278; 800/279; 800/300; 800/301; 800/302; 800/303; 4335/414
(58) Field of Search .............................. 800/317, 317.3, 800/317.5, 260, 265, 278, 279, 300, 301, 302, 303; 435/414

(56) References Cited

PUBLICATIONS

Cytogenetics of flower modification of a cytoplasmic male-sterile tobacco D.U. Gerstel et al. 1980 Genetics 96:223–225.*

The effect of removing Leaf Surface Components with Acetone from Immunized and Nonimmuzied Resistant Tobacco Plants on Their Susceptibility to Blue Mold. S.Tuzun et al. 1989 The American Phytopathological Society vol. 79, No 10 1024–1027.*

Brake et al.; "Use of Marker Assisted Selection to Screen for Blue Mold Resistant in Burley Tobacco," *Agronomy/Phytopatholoy Programme for Accompanying Persons*, Coresta, Lisbon, Portugal (Oct. 16–19, 2000).

Milla; Thesis—"Identification of RAPD Markers Linked to Blue Mold Resistance in Tobacco," *NCSU—Department of Crop Science*, Raleigh, NC (1998).

Rufty; "Genetics of Host Resistance to Tobacco Blue Mold," Chapter 5, *Blue Mold of Tobacco* (American Phytopathological Society Press) 141–164 (1989).

Rufty et al., "Registration of NC–BMR 42 and NC–BMR 90 Germplasm Lines of Tabacco," *Crop Science* 30:1 241–242 (1990).

Wernsman et al.; "Tobacco" Chapter 17, *Cultivar Development Crop Species* 669–698 (1987).

* cited by examiner

*Primary Examiner*—Anne Kubelik
*Assistant Examiner*—Annette H Para
(74) *Attorney, Agent, or Firm*—Myers Bigel Sibley & Sajovec, P.A.

(57) ABSTRACT

The present invention relates to a novel tobacco cultivar designated NC 2000, which is resistant to blue mold caused by the fungus *Peronospora tabacina* Adam. The invention provides seeds of the cultivar NC 2000, plants and parts thereof of the cultivar NC 2000, a tissue culture derived from the cultivar NC 2000, hybrids produced from cultivar NC 2000 and lines derived from cultivar NC 2000, as well as genetically modified forms of the foregoing plants and tissue culture. Also provided are methods of producing cultivar NC 2000 plants, cultivar NC 2000 hybrid plants, and tobacco lines derived from cultivar NC 2000.

34 Claims, 2 Drawing Sheets

SEQUENCE LISTING

<160> NUMBER OF SEQ ID NOS: 17

<210> SEQ ID NO 1
<211> LENGTH: 10
<212> TYPE: DNA
<213> ORGANISM: Artificial Sequence
<220> FEATURE:
<223> OTHER INFORMATION: Coupling marker

<400> SEQUENCE: 1
tcgttcaccc                                                          10

<210> SEQ ID NO 2
<211> LENGTH: 10
<212> TYPE: DNA
<213> ORGANISM: Artificial Sequence
<220> FEATURE:

-continued

<223> OTHER INFORMATION: Repulsion marker

<400> SEQUENCE: 2
gtgtcagtgg                                                                 10

<210> SEQ ID NO 3
<211> LENGTH: 10
<212> TYPE: DNA
<213> ORGANISM: Artificial Sequence
<220> FEATURE:
<223> OTHER INFORMATION: Coupling marker

<400> SEQUENCE: 3
tgcgctcctc                                                                 10

<210> SEQ ID NO 4
<211> LENGTH: 10
<212> TYPE: DNA
<213> ORGANISM: Artificial Sequence
<220> FEATURE:
<223> OTHER INFORMATION: Coupling marker

<400> SEQUENCE: 4
ctcaccgtcc                                                                 10

<210> SEQ ID NO 5
<211> LENGTH: 10
<212> TYPE: DNA
<213> ORGANISM: Artificial Sequence
<220> FEATURE:
<223> OTHER INFORMATION: Coupling marker

<400> SEQUENCE: 5
aacgcgtcgg                                                                 10

<210> SEQ ID NO 6
<211> LENGTH: 10
<212> TYPE: DNA
<213> ORGANISM: Artificial Sequence
<220> FEATURE:
<223> OTHER INFORMATION: Coupling marker

<400> SEQUENCE: 6
gtctacggca                                                                 10

<210> SEQ ID NO 7
<211> LENGTH: 10
<212> TYPE: DNA
<213> ORGANISM: Artificial Sequence
<220> FEATURE:
<223> OTHER INFORMATION: Coupling marker

<400> SEQUENCE: 7
acagggtga                                                                  10

<210> SEQ ID NO 8
<211> LENGTH: 10
<212> TYPE: DNA
<213> ORGANISM: Artificial Sequence
<220> FEATURE:
<223> OTHER INFORMATION: Coupling marker

<400> SEQUENCE: 8
agcagcgtgg                                                                 10

-continued

```
<210> SEQ ID NO 9
<211> LENGTH: 10
<212> TYPE: DNA
<213> ORGANISM: Artificial Sequence
<220> FEATURE:
<223> OTHER INFORMATION: Coupling marker

<400> SEQUENCE: 9
gggccacgct                                                           10

<210> SEQ ID NO 10
<211> LENGTH: 10
<212> TYPE: DNA
<213> ORGANISM: Artificial Sequence
<220> FEATURE:
<223> OTHER INFORMATION: Repulsion marker

<400> SEQUENCE: 10
atgttccagg                                                           10

<210> SEQ ID NO 11
<211> LENGTH: 10
<212> TYPE: DNA
<213> ORGANISM: Artificial Sequence
<220> FEATURE:
<223> OTHER INFORMATION: Repulsion marker

<400> SEQUENCE: 11
gggtgaaccg                                                           10

<210> SEQ ID NO 12
<211> LENGTH: 10
<212> TYPE: DNA
<213> ORGANISM: Artificial Sequence
<220> FEATURE:
<223> OTHER INFORMATION: Coupling marker

<400> SEQUENCE: 12
ggatctatgc                                                           10

<210> SEQ ID NO 13
<211> LENGTH: 10
<212> TYPE: DNA
<213> ORGANISM: Artificial Sequence
<220> FEATURE:
<223> OTHER INFORMATION: Coupling marker

<400> SEQUENCE: 13
cacccctgc                                                            10

<210> SEQ ID NO 14
<211> LENGTH: 10
<212> TYPE: DNA
<213> ORGANISM: Artificial Sequence
<220> FEATURE:
<223> OTHER INFORMATION: Coupling marker

<400> SEQUENCE: 14
tagagactcc                                                           10

<210> SEQ ID NO 15
<211> LENGTH: 10
<212> TYPE: DNA
<213> ORGANISM: Artificial Sequence
<220> FEATURE:
<223> OTHER INFORMATION: Coupling marker
```

-continued

```
<400> SEQUENCE: 15
cgccgctcct                                                              10

<210> SEQ ID NO 16
<211> LENGTH: 10
<212> TYPE: DNA
<213> ORGANISM: Artificial Sequence
<220> FEATURE:
<223> OTHER INFORMATION: Coupling marker

<400> SEQUENCE: 16
tttgccgccc                                                              10

<210> SEQ ID NO 17
<211> LENGTH: 10
<212> TYPE: DNA
<213> ORGANISM: Artificial Sequence
<220> FEATURE:
<223> OTHER INFORMATION: Coupling marker

<400> SEQUENCE: 17
gtgataagcc                                                              10
```

TOBACCO CULTIVAR NC 2000

RELATED APPLICATION INFORMATION

This application claims the benefit of U.S. Provisional Application No. 60/323,908, filed Sep. 21, 2001, the disclosure of which is incorporated by reference herein in its entirety.

FIELD OF THE INVENTION

The present invention relates to tobacco breeding, in particular, to a new tobacco cultivar designated NC 2000 that is resistant to blue mold caused by the fungus *Peronospora tabacina* Adam.

BACKGROUND OF THE INVENTION

Tobacco (*Nicotiana tabacum* L.) is an important commercial crop in the United States as well as in other countries. Blue mold is one of the most significant foliar diseases of tobacco. When weather conditions are favorable, the disease spreads rapidly and attacks plants throughout the growing season. It can completely destroy transplants in the bed. In the field, the presence of the pathogen can be seen as brown necrotic spots on the leaves or as a systemic infection.

Control of the pathogen can be achieved by two means: the use of fungicides and the introduction of resistant varieties. The development of fungicide resistant strains of the fungus has increased the need for resistant varieties. Naturally occurring host resistance to *Peronospora tabacina* exists among wild *Nicotiana* species mainly of Australian origin, where the pathogen is endemic. Transfer of resistance into cultivated tobacco from various sources has been successfully achieved via interspecific hybridization. The most widely used sources are *N. debneyi* accessions. Commercially grown burley cultivars are either susceptible or very susceptible to the disease, with the exception of TN 90, which is relatively tolerant, but is not resistant.

Accordingly, it would be desirable to provide a tobacco cultivar that demonstrates blue mold resistance.

There are numerous stages in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The aim is to combine in a single variety an improved combination of desirable traits from the parental germplasm. These important traits may include higher yield, resistance to diseases and insects, better stems and roots, tolerance to drought and heat, improved nutritional quality, and better agronomic quality.

Choice of breeding or selection methods depends on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences the choice of breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goals and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are typically tested and compared to appropriate standards in environments representative of the commercial target area(s) for three or more years. The best lines are candidates for new commercial cultivars; those still deficient in a few traits may be used as parents to produce new populations for further selection.

An important task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of a tobacco breeding program is to develop new, unique and superior tobacco cultivars and hybrids. The breeder typically initially selects and crosses two or more parental lines, followed by repeated selfing and selection, producing many new genetic combinations. In tobacco, completely homozygous doubled-haploid plants may also be generated (Burk et al., (1979) *Science* 206:585). The breeder can theoretically generate billions of different genetic combinations via crossing, selfing and mutations.

Each year, the plant breeder selects the germplasm to advance to the next generation. This germplasm is grown under different geographical, climate and soil conditions, and further selections are then made, both during and at the end of the growing season. The cultivars which are developed are unpredictable. This unpredictability is because the breeder's selection occurs in unique environments and there are millions of different possible genetic combinations being generated. A breeder of ordinary skill in the art cannot predict the final resulting lines, except in a very general fashion. The same breeder cannot produce the same cultivar twice by using the exact same original parents and the same selection techniques. This unpredictability results in the expenditure of large amounts of research monies to develop superior new tobacco cultivars.

The development of new tobacco hybrids involves the development and selection of tobacco breeding lines, the crossing of these breeding lines and selection of superior hybrid crosses. The hybrid seed is produced by manual crosses between selected male-fertile parents or by using male sterility systems. Hybrid combinations are identified and developed on the basis of certain single gene traits such as leaf size or color, flower color, disease resistance or herbicide resistance, and the like, which are expressed in a hybrid. Additional data, such as yield and quality traits, on parental lines as well as the phenotype of the hybrid influence the breeder's decision to continue with the specific hybrid cross."

Pedigree breeding and recurrent selection breeding methods are used to develop true breeding cultivars from breeding populations. Breeding programs combine desirable traits from two or more cultivars or various broad-based sources into breeding pools from which cultivars are developed by selfing or alternatively, by creating doubled-haploids, and selection of desired phenotypes. The new cultivars are evaluated to determine which have commercial potential.

Pedigree breeding is commonly used for the improvement of self-pollinating crops and parental lines for hybrids. Two parents which possess favorable, complementary traits are crossed to produce an $F_1$. An $F_2$ population is produced by selfing one or several $F_1$ plants. Selection of the best individuals may begin in the $F_2$ population; then, beginning in the $F_3$, the best individuals in the families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines in each generation due to failure of some seeds to germinate or some plants to produce at least one seed. As a result, not all of the $F_2$ plants originally sampled in the population will be represented by a progeny when generation advance is completed.

In a multiple-seed procedure, tobacco breeders harvest seeds from one or more flowers from each plant in a population and pool them to form a bulk. Part of the bulk is used to plant the next generation and part is put in reserve. The procedure has been referred to as modified single-seed descent technique.

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, the processor and the consumer, for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Maternal haploids can be obtained by pollination of plants of *N. tabacum* with *N. africana*. Numerous seeds develop in fruits from this cross, but germinating interspecific hybrid seedlings are highly lethal (99.9%). Surviving $F_1$ plants consist of mixtures of aneuploid interspecific hybrids and maternal haploids. The chromosomes of the maternal haploids are derived from the *N. tabacum* female plant. The procedure is very simple, but requires technical skill to distinguish phenotypically the aneuploid interspecific hybrids from maternal haploids in seedling stages. Environmental effects on tobacco females crossed with *N. africana* pollen greatly influence the number of haploids obtained per capsule. One to three haploid plants frequently can be obtained from a capsule of a tobacco× *N. africana* cross when the tobacco female is grown in the field. Haploid numbers per pollination of greenhouse-grown tobacco are five to ten times lower. Chromosome-doubled haploids obtained by this technique are superior to ADH lines from the same parental sources and more closely resemble the performance of conventionally developed inbred genotypes.

Methods of tobacco breeding are discussed in detail in Wernsman, E. A., and Rufty, R. C. 1987. Chapter Seventeen. Tobacco. Pages 669–698 In: Cultivar Development. Crop Species. W. H. Fehr (ed.), MacMillan Publishing Go., Inc., New York, N.Y. 761 pp.

SUMMARY OF THE INVENTION

The present invention relates to a new and distinctive doubled-haploid tobacco cultivar designated NC 2000, which is the result of years of careful breeding and selection, and is highly resistant to blue mold. As far as the inventor is aware, NC 2000 is the first blue mold resistant burley cultivar.

The invention further provides seeds of the cultivar NC 2000, plants of the cultivar NC 2000, tissue culture comprising tissue, callus, cells or protoplasts of the cultivar NC 2000, hybrids having a cultivar NC 2000 parent or ancestor, and NC 2000 derived tobacco plants, as well as genetically modified (e.g., by conventional breeding or genetic engineering techniques) forms of the foregoing plants and tissue culture. The present invention further provides methods of producing a tobacco plant by crossing the NC 2000 cultivar with itself or a different tobacco line. The invention further relates to methods for producing other tobacco cultivars or breeding lines derived from cultivar NC 2000.

These and other aspects of the invention are set forth in more detail in the description of the invention below.

DETAILED DESCRIPTION OF THE INVENTION

Figure 1:
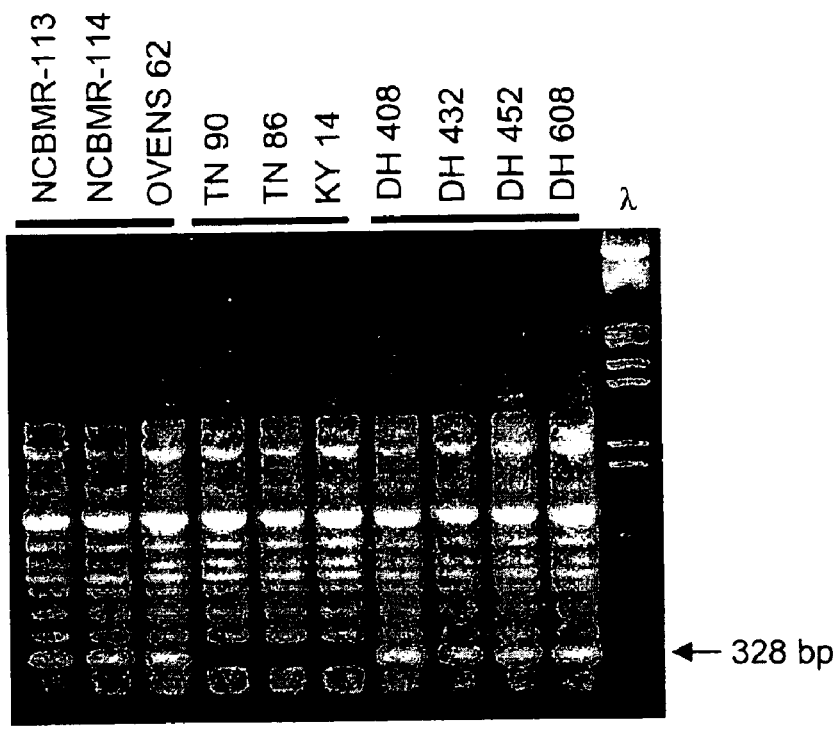
FIGS. 1 and 2. RAPD reaction of individual tobacco varieties (controls) and doubled haploid lines.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

As used herein, a tobacco plant that is "resistant" to blue mold or blue mold "resistance" is intended to indicate that the plant has a significantly reduced size and/or incidence of lesions induced by the pathogen *Peronospora tabacina* Adam as compared with a control susceptible variety (e.g., KY 14 or the like) under conditions of infestation. Resistance may be evaluated by any suitable method known in the art, e.g., by determining the percentage leaf area damage induced by blue mold. The term "resistant/resistance" is not intended to indicate that the plant is absolutely immune from blue mold. Those skilled in the art will appreciate that the degree of resistance may be assessed with respect to a plurality or even an entire field of plants. A tobacco strain may be considered "resistant" to blue mold if the overall incidence and/or size of lesions is reduced, even if particular, individual, plants may be susceptible to disease.

In embodiments of the invention, the blue mold resistant plants of the invention have one or more (e.g., two or more, three or more, four and more, etc.) of the coupling markers listed in Table 5. Likewise, in embodiments of the invention, the blue mold resistant tobacco plants lack one or more of the repulsion markers listed in Table 5. In particular embodiments, the tobacco plants of the invention have all of the coupling markers in Table 5 and/or lack all of the repulsion markers of Table 5.

Description of the Variety.

Burley Tobacco Cultivar NC 2000, tested and developed as DH 408, is a doubled-haploid line derived from the cross of NC BMR-113 (a blue mold resistant germplasm line released by the North Carolina Agricultural Research Service in 1992) X KY 14. Doubled-haploid lines were obtained from $F_1$ hybrids of this cross using the *N. africana* method for generating maternal haploids (Burk et al., (1979) *Science* 206:585) followed by chromosome doubling using the in vitro mid-vein culture technique (Kasperbauer and Collins, (1972) *Crop. Sci.* 12:98).

Several hundred doubled-haploid lines ($F_1$-derived) were grown. The plants were bagged to prevent cross-pollination and the seeds collected. Five plants from each doubled-haploid line were grown, the plants bagged, and the seeds collected and pooled for each line for two consecutive years prior to field trials.

In 1992 through 1996, the doubled-haploid lines were field tested for blue mold resistance in Papantla, Veracruz, Mexico, where blue mold is endemic. As a result of the field test results, line DH 408 was selected for its stable, uniform and high-level of resistance to blue mold, and was eventually re-designated as NC 2000. NC 2000 was further characterized in field studies at the Mountain Research Station (Waynesville, N.C.) and the Upper Mountain Research Station (Laurel Springs, N.C.) and in the 1998 Regional Burley Variety Evaluation Test.

NC 2000 is highly resistant to blue mold caused by the fungus *Peronospora tabacina* Adam. Percent leaf area damage ratings of NC 2000 to blue mold are significantly lower than disease values of any commercial burley cultivar evaluated for this trait. Because the NC 2000 cultivar is not completely immune to blue mold, a minimum number of fungicide applications may be necessary during prolonged cool and wet periods, which are highly conducive to blue mold development.

NC 2000 has all of the coupling markers and lacks all of the repulsion markers shown in Table 5.

NC 2000 is also resistant to tobacco mosaic virus (TMV) and wildfire (*Pseudomonas syringae* pv. *tabaci*), but susceptible to black shank (races 1 and 0), black root rot, and the polyvirus complex.

Yielding ability of NC 2000 compares well with commercial cultivars and has a weighted grade index equivalent to VA 509 and modestly higher than KY 14. NC 2000 has acceptable levels of nicotine and total alkaloids. Results of the 1998 Regional Burley Evaluation Test indicate that NC 2000 meets minimum quality standards and smoke flavor is acceptable.

NC 2000 is a pure doubled-haploid line selected from a single plant and, therefore, is completely homozygous. The resistance of NC 2000 to tobacco blue mold caused by the fungus *Peronospora tabacina* Adam has remained stable and uniform within commercially acceptable limits over at least eight generations. No variants in blue mold resistance have been observed to date.

Additional morphological and physiological characterization of cultivar NC 2000 is found in Appendix A, which is attached hereto. Although NC 2000 is a pure line derived from a single doubled-haploid plant, NC 2000 shows about 5% of off-type plants, primarily attributable to variations in the leaf shape and leaf angle.

Other Embodiments of the Invention

The present invention also encompasses hybrid plants produced from tobacco cultivar NC 2000, tobacco plants derived from NC 2000, and NC 2000 plants comprising a gene that has been introduced therein by traditional breeding or genetic engineering techniques, and seeds, plant parts, and tissue cultures of the foregoing plants, as well as methods of producing the plants of the invention.

I. Male Sterile Plants.

Tobacco can be bred by both self-pollination and cross-pollination techniques. Individual tobacco flowers have both male and female reproductive organs, and tobacco is naturally self-pollinating. It is known in the art that it is often advantageous to create male sterile/female fertile plants so that self-pollination can be controlled.

Male sterile tobacco plants may be produced by any method known in the art. Methods of producing male sterile tobacco are described in Wernsman, E. A., and Rufty, R. C. 1987. Chapter Seventeen. Tobacco. Pages 669–698 In: Cultivar Development. Crop Species. W. H. Fehr (ed.), MacMillan Publishing Go., Inc., New York, N.Y. 761 pp.

A reliable method of controlling male fertility in plants offers the opportunity for improved plant breeding. This is especially true for development of tobacco hybrids, which typically relies upon some sort of male sterility system. There are several options for controlling male fertility available to breeders, such as: manual or mechanical emasculation, cytoplasmic male sterility, genetic male sterility, gametocides and the like. In one approach, alternate strips of two tobacco lines are planted in a field, and the male portions of flowers are removed from one of the lines (female). Providing that there is sufficient isolation from sources of foreign tobacco pollen, the emasculated plant will be fertilized only from the other line (male), and the resulting seed is therefore hybrid and will form hybrid plants.

The laborious, and occasionally unreliable, mechanical emasculation process can be avoided by using cytoplasmic male-sterile (CMS) lines. Plants of a CMS line are male sterile as a result of factors resulting from the cytoplasmic, as opposed to the nuclear, genome. Thus, this characteristic is inherited exclusively through the female parent in tobacco plants, since only the female provides cytoplasm to the fertilized seed. CMS plants are fertilized with pollen from another line that is not male-sterile. Pollen from the second line may or may not contribute genes that make the hybrid plants male-fertile.

Alternative approaches of conferring genetic male sterility are also suitable, such as multiple mutant genes at separate locations within the genome that confer male sterility and chromosomal translocations.

Still further methods of conferring genetic male sterility use a variety of approaches such as delivering into the plant a gene encoding a cytotoxic substance associated with a male tissue specific promoter or an antisense system in which a gene critical to male fertility is identified and an antisense to that gene is inserted in the plant.

Another system useful in controlling male fertility makes use of gametocides. Gametocides do not involve a genetic system, but rather a topical application of chemicals. These chemicals affect cells that are critical to male fertility. The application of these chemicals affects fertility in the plants only for the growing season in which the gametocide is applied (see U.S. Pat. No. 4,936,904). Application of the gametocide, timing of the application and genotype specificity often limit the usefulness of the approach.

II. Hybrid Production.

The use of male sterile lines is but one factor in the production of tobacco hybrids. The development of tobacco hybrids involves, in general, the development of completely homozygous lines, the crossing of these lines, and the evaluation of the crosses. In the case of tobacco, a completely homozygous line may be an inbred or a doubled-haploid line.

Pedigree breeding and recurrent selection breeding methods are typically used to develop inbred lines from breeding populations. Breeding programs combine the genetic backgrounds from two or more inbred lines or various other germplasm sources into breeding pools from which new inbred lines are developed by selfing and selection of desired phenotypes. The new inbreds are crossed with other inbred lines or doubled-haploid lines, and the hybrids from these crosses are evaluated to determine which of those have commercial potential.

Doubled-haploid breeding is a more rapid method for producing completely homozygous tobacco plants (Burk et al., (1979) *Science* 206:585). Haploid plants or cultures of haploid cells or tissues are produced and chromosome doubling is induced, for example, by colchicine treatment or by the midvein culture technique. Doubled-haploid plants are regenerated following chromosomal doubling.

Pedigree breeding starts with the crossing of two genotypes, each of which may have one or more desirable characteristics that is lacking in the other or which complements the other. If the two original parents do not provide all the desired characteristics, other sources can be included in the breeding population. In the pedigree method, superior plants are selfed and selected in successive generations. In the succeeding generations, the heterozygous condition gives way to homogeneous lines as a result of self-pollination and selection. Typically in the pedigree method of breeding, five or more generations of selfing and selection is practiced.

A single cross tobacco hybrid results from the cross of two inbred or doubled-haploid lines, or from the cross of an inbred with a doubled-haploid line, each of the parents having a genotype that complements the genotype of the other. The hybrid progeny of the first generation is designated $F_1$. Preferred F1 hybrids may be more vigorous than their inbred parents. This hybrid vigor, or heterosis, can be manifested in many polygenic traits, including increased vegetative growth and increased yield.

In general, the development of a tobacco hybrid involves three steps: (1) the selection of plants from various germplasm pools for initial breeding crosses; (2) the selfing of the selected plants from the breeding crosses for several generations to produce a series of inbred lines, which, although different from each other, breed true and are highly uniform and/or the production of a series of doubled-haploid lines; and (3) crossing the selected inbred and/or doubled-haploid lines with different inbred/doubled-haploid lines to produce the hybrid progeny ($F_1$). A consequence of the homozygosity and homogeneity of the inbred and/or doubled-haploid lines is that the hybrid between a defined pair of inbreds/doubled-haploids will always be the same. Once the parents that give a superior hybrid have been identified, the hybrid seed can be reproduced indefinitely as long as the homogeneity of the parents is maintained.

A single cross hybrid is produced when two lines are crossed to produce the $F_1$ progeny. A double cross hybrid is produced from four inbred and/or doubled-haploid lines crossed in pairs (A×B and C×D) and then the two $F_1$ hybrids are crossed again (A×B)×(C×D). Much of the hybrid vigor exhibited by $F_1$ hybrids is generally lost in the next generation ($F_2$). Consequently, seed from hybrids is not typically used for planting stock.

As described above, hybrid seed production regimes generally use male sterile/female fertile parent plants. Incomplete removal or inactivation of the pollen provides the potential for self pollination. This inadvertently self pollinated seed may be unintentionally harvested and packaged with hybrid seed. Once the seed is planted, it is possible to identify and select these self pollinated plants due to their decreased vigor. These self-pollinated plants will be genetically equivalent to the female inbred line used to produce the hybrid. Female selfs are identified by their less vigorous, appearance for vegetative and/or reproductive characteristics as is known in the art.

Identification of these self-pollinated lines can also be accomplished through molecular marker analyses. Through these technologies, the homozygosity of the self-pollinated line can be verified by analyzing allelic composition at various loci along the genome.

III. Evaluation of Plants for Homozygosity and Phenotypic Stability.

It is desirable and advantageous for a tobacco cultivar to be highly homogeneous, homozygous and phenotypically uniform and stable for use as a commercial cultivar. In the case of double-haploids, these plants are generated so as to be completely homozygous and uniform. In the case of inbreds or other lines, there are many analytical methods available to determine the homozygotic and phenotypic stability of the variety.

The oldest and most traditional method of analysis is the observation of phenotypic traits. The data is usually collected in field experiments over the life of the tobacco plants to be examined. Phenotypic characteristics most often observed are for traits associated with seed yield, disease resistance, maturity, plant height, flower color, leaf color, leaf yield, leaf size, leaf angle, and concentration of chemical components such as nicotine, total alkaloids or reducing sugars.

In addition to phenotypic observations, the genotype of a plant can also be examined. There are many laboratory-based techniques available for the analysis, comparison and characterization of plant genotypes; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites.

As described in Examples 2 and 3, the tobacco BMR locus, which confers resistance to blue mold, has been found to be linked to 21 markers (Table 5). Some of these markers (UBC-149, UBC-180, UBC-534, UBC-544, UBC-610, UBC-240) are particularly reliable for determining whether a plant is resistant to blue mold. As described above, in embodiments of the invention, the claimed tobacco plant has one or more of the coupling markers and/or lacks one or more of the repulsion markers shown in Table 5.

The presence or absence of the marker in the plant genotype may be determined by any method known in the art. For example, the marker sequence (or its complement) may be used as a hybridization probe, e.g., for Southern or in situ analysis of genomic DNA. Typically, however, due to greater ease and sensitivity, an amplification method, such as PCR will be used to detect the presence or absence of the marker in the plant genotype.

The molecular markers disclosed herein can be used in any method of nucleic acid amplification known in the art. Such methods include but are not limited to Polymerase Chain Reaction (PCR; described in U.S. Pat. Nos. 4,683, 195, 4,683,202, 4,800,159, 4,965,188), Strand Displacement Amplification (SDA; described by G. Walker et al., *Proc. Nat Acad. Sci. USA* 89, 392 (1992); G. Walker et al., *Nucl. Acids Res.* 20, 1691 (1992); U.S. Pat. No. 5,270,184), thermophilic Strand Displacement Amplification (tSDA; EP 0 684 315 to Frasier et al.), Self-Sustained Sequence Replication (3SR; J. C. Guatelli et al., *Proc Natl. Acad. Sci. USA* 87,1874–78 (1990)), Nucleic Acid Sequence-Based Amplification (NASBA; U.S. Pat. No. 5,130,238 to Cangene), the Qβ replicase system (P. Lizardi et al., *BioTechnology* 6, 1197 (1988)), or transcription based amplification (D. Y. Kwoh et al., *Proc. Natl. Acad. Sci. USA* 86, 1173–77 (1989)).

IV. Transfer of Traits into Tobacco Cultivar NC 2000.

Genetic variants of NC 2000 that are naturally-occurring or created through traditional breeding methods using cultivar NC 2000 are also intended to be within the scope of this invention. In particular embodiments, the invention encompasses plants of cultivar NC 2000 and parts thereof further comprising one or more additional traits, in particular, specific, single gene transferred traits. Examples of traits that may be transferred include, but are not limited to, herbicide resistance, disease resistance (e.g., bacterial fungal or viral disease), nematode resistance, yield enhancement, improved nutritional quality (e.g., oil starch and protein content or quality), altered chemical composition (e.g., nicotine, total alkaloids, reducing sugars), improved leaf characteristics (color, shape, size, number, angle), or other agronomically important traits.

Such traits may be introgressed into cultivar NC 2000 from another tobacco cultivar or may be directly transformed into cultivar NC 2000 (discussed below). Preferably, one or more new traits are transferred to cultivar NC 2000, or, alternatively, one or more traits of cultivar NC 2000 are altered or substituted. The introgression of the trait(s) into cultivar NC 2000 may be achieved by any method of plant breeding known in the art, for example, pedigree breeding, backcrossing, doubled-haploid breeding, and the like (see, Wernsman, E. A., and Rufty, R. C. 1987. Chapter Seventeen. Tobacco. Pages 669–698 In: Cultivar Development. Crop Species. W. H. Fehr (ed.), MacMillan Publishing Go., Inc., New York, N.Y. 761 pp.).

The laboratory-based techniques described above, in particular RFLP and SSR, can be used in such backcrosses to identify the progenies having the highest degree of genetic identity with the recurrent parent. This permits one to accelerate the production of tobacco cultivars having at least 90%, preferably at least 95%, more preferably at least 99% genetic identity with the recurrent parent, yet more preferably genetically identical to the recurrent parent, and further comprising the trait(s) introgressed from the donor patent. Such determination of genetic identity can be based on molecular markers used in the laboratory-based techniques described above.

The last backcross generation is then selfed to give pure breeding progeny for the gene(s) being transferred. The resulting plants generally have essentially all of the morphological and physiological characteristics of cultivar NC 2000, in addition to the trait(s) (e.g., one or more single gene traits) transferred to the inbred. The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Those skilled in the art will appreciate that the tobacco genes described below in connection with tobacco plants produced by genetic engineering techniques may also be introduced into cultivar NC 2000 by conventional breeding methods.

V. Transformation of Tobacco.

With the advent of molecular biological techniques that have allowed the isolation and characterization of genes that encode specific protein products, scientists in the field of plant biology developed a strong interest in engineering the genome of plants to contain and express foreign genes, or additional, or modified versions of native or endogenous genes (perhaps driven by different promoters) in order to alter the traits of a plant in a specific manner. Such foreign, additional and/or modified genes are referred to herein collectively as "transgenes." The term "transgene," as used herein, is not necessarily intended to indicate that the foreign gene is from a different plant species. For example, the transgene may be a particular allele derived from another tobacco line or may be an additional copy of an endogenous gene. Over the last fifteen to twenty years several methods for producing transgenic plants have been developed. Therefore, in particular embodiments, the present invention also encompasses transformed versions of the tobacco cultivar NC 2000.

Plant transformation involves the construction of an expression vector that will function in plant cells. Such a vector comprises DNA or RNA comprising a gene under control of, or operatively linked to, a regulatory element (for example, a promoter). The expression vector may contain one or more such operably linked gene/regulatory element combinations. The vector(s) may be in the form, e.g., of a plasmid or a virus, and can be used, alone or in combination with other vectors, to provide transformed tobacco plants, using transformation methods as described below to incorporate transgenes into the genetic material of the tobacco plant(s).

Any transgene(s) known in the art may be introduced into a tobacco plant, tissue, cell or protoplast according to the present invention, e.g., to improve commercial or agronomic traits, herbicide resistance, disease resistance (e.g., to a bacterial fungal or viral disease), nematode resistance, yield enhancement, nutritional quality (e.g., oil starch and protein content or quality), leaf characteristics (color, shape, size, number, angle), and altered reproductive capability (e.g., male sterility) or chemical composition (e.g., nicotine, total alkaloids, reducing sugars). Alternatively, a transgene may be introduced for the production of recombinant proteins (e.g., enzymes) or metabolites.

In particular embodiments of the invention a transgene conferring glyphosate resistance is introduced into the tobacco plant. Alternatively, a transgene conferring disease resistance is introduced. Exemplary transgenes are those conferring resistance to Tobacco Mosaic Virus, Tobacco etch virus, Tobacco vein mottling virus, Black root rot, Potato Virus Y, Bacterial wilt (*Pseudomonas solanacearum*), Black shank fungus (*Phythophthora parasitica*), wild fire (*Pseudomonas syringae*), and root knot nematodes.

In other embodiments, the transgene encodes an antisense RNA or any other non-translated RNA as is known in the art.

A. Expression Vectors for Tobacco Transformation.

1. Marker Genes.

Expression vectors typically include at least one genetic marker, operably linked to a regulatory element (a promoter, for example) that allows transformed cells containing the marker to be either recovered by negative selection, i.e., inhibiting growth of cells that do not contain the selectable marker gene, or by positive selection, i.e., screening for the product encoded by the genetic marker. Many commonly used selectable marker genes for plant transformation are well known in the transformation art, and include, for example, genes that code for enzymes that metabolically detoxify a selective chemical agent which may be an antibiotic or a herbicide, or genes that encode an altered target which is insensitive to the inhibitor. A few positive selection methods are also known in the art.

One commonly used selectable marker gene for plant transformation is the neomycin phosphotransferase II (npfII) gene, isolated from transposon Tn5, which when placed under the control of plant regulatory signals confers resistance to kanamycin (Fraley et al., (1983) *Proc. Natl. Acad. Sci. U.S.A.*, 80: 4803). Another commonly used selectable marker gene is the hygromycin phosphotransferase gene, which confers resistance to the antibiotic hygromycin (Vanden Elzen et al., (1985) *Plant Mol. Biol.*, 5: 299).

Additional selectable marker genes of bacterial origin that confer resistance to antibiotics include gentamycin acetyl transferase, streptomycin phosphotransferase, aminoglycoside-3'-adenyl transferase, the bleomycin resistance determinant (Hayford et al., (1988) *Plant Physiol.* 86: 1216; Jones et al., (1987) *Mol. Gen. Genet.*, 210: 86; Svab et al., (1990) *Plant Mol. Biol.* 14: 197; Hille et al., (1986) *Plant Mol. Biol.* 7: 171). Other selectable marker genes confer resistance to herbicides such as glyphosate, glufosinate or bromoxynil (Comai et al., (1985) *Nature* 317: 741; Gordon-Kamm et al., (1990) *Plant Cell* 2: 603; and Stalker et al., (1988) *Science* 242: 419).

Other selectable marker genes for plant transformation are not of bacterial origin. These genes include, for example, mouse dihydrofolate reductase, plant 5eno/pyruvylshikimate-3-phosphate synthase and plant acetolactate synthase (Eichholtz et al., (1987) *Somatic Cell Mol. Genet.* 13: 67; Shah et al., (1986) *Science* 233: 478; Charest et al., (1990) *Plant Cell Rep.* 8: 643).

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression. Commonly used genes for screening presumptively transformed cells include β-glucuronidase (GUS), β-galactosidase, luciferase and chloramphenicol acetyltransferase (Jefferson, R. A., (1987) *Plant Mol. Biol. Rep.* 5: 387; Teeri et al., (1989) *EMBO J.* 8: 343; Koncz et al., (1987) *Proc. Natl. Acad. Sci. U.S.A.* 84:131; De Block et al., (1984) *EMBO J.* 3: 1681).

In vivo methods for visualizing GUS activity that do not require destruction of plant tissue are also available (Molecular Probes Publication 2908, Imagene Green™, p. 1–4 (1993) and Naleway et al., (1991) *J. Cell Biol.* 115: 15). However, these in vivo methods for visualizing GUS activity have not proven useful for recovery of transformed cells because of low sensitivity, high fluorescent backgrounds, and limitations associated with the use of luciferase genes as selectable markers.

In addition, a gene encoding Green Fluorescent Protein (GFP) has been utilized as a marker for gene expression in prokaryotic and eukaryotic cells (Chalfie et al., (1994) *Science* 263: 802). GFP and mutants of GFP may be used as screenable markers.

2. Promoters.

Genes included in expression vectors are typically driven by a nucleotide sequence comprising a regulatory element, for example, a promoter. Several types of promoters are now well known in the transformation art, as are other regulatory elements that can be used alone or in combination with promoters.

As used herein "promoter" includes reference to a region of DNA (or RNA) upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred". Promoters which initiate transcription only in certain tissues are referred to as "tissue-specific". A "cell type" specific promoter primarily drives expression in certain cell types in one or more organs, for example, vascular cells in roots or leaves. An "inducible" promoter is a promoter which is under environmental control. Examples of environmental conditions that may effect transcription by inducible promoters include anaerobic conditions or the presence of light. Tissue-specific, tissue-preferred, cell type specific, and inducible promoters are included in the class of "non-constitutive" promoters. A "constitutive" promoter is a promoter which is active under most environmental conditions.

(A) Inducible Promoters.

An inducible promoter may be operably linked to a gene for expression in tobacco. Optionally, the inducible promoter is operably linked to a nucleotide sequence encoding a signal sequence which is operably linked to a gene for expression in tobacco. With an inducible promoter the rate of transcription increases in response to an inducing agent.

Any inducible promoter can be used in the instant invention (see, Ward et al., (1993) *Plant Mol. Biol.* 22: 361). Exemplary inducible promoters include, but are not limited to, that from the ACEI system which responds to copper (Melt et al., (1993) *PNAS* 90: 4567); the In2 gene from maize which responds to benzenesulfonamide herbicide safeners (Hershey et al., (1991) *Mol. Gen. Genetics* 227: 229 and Gatz et al., (1994) *Mol. Gen. Genetics* 243: 32) or the Tet repressor from Tn10 (Gatz et al., (1991) *Mol. Gen. Genet.* 227: 229). A particularly preferred inducible promoter is a promoter that responds to an inducing agent to which plants do not normally respond. An exemplary inducible promoter is the inducible promoter from a steroid hormone gene, the transcriptional activity of which is induced by a glucocorticosteroid hormone (Schena et al., (1991) *Proc. Natl. Acad. Sci. U.S.A.* 88: 421).

(B) Constitutive Promoters.

In other embodiments, a constitutive promoter is operably linked to a gene for expression in tobacco or the constitutive promoter is operably linked to a nucleotide sequence encoding a signal sequence which is operably linked to a gene for expression in tobacco.

Many different constitutive promoters can be utilized in the instant invention. Exemplary constitutive promoters include, but are not limited to, the promoters from plant viruses such as the 35S promoter from CaMV (Odell et al., (1985) *Nature* 313: 810) and the promoters from such genes as rice actin (McElroy et al., (1990) *Plant Cell* 2: 163); ubiquitin (Christensen et al., (1989) *Plant Mol. Biol* 12: 619 and Christensen et al., (1992) *Plant Mol. Biol.* 18: 675); pEMU (Last et al., (1991) *Theor. Appl. Genet.* 81: 581); MAS (Velten et al., (1984) *EMBO J.* 3: 2723) and maize H3 histone (Lepelit et al., (1992) *Mol. Gen. Genet.* 231: 276 and Atanassova et al., (1992) *Plant Journal* 2: 291).

The ALS promoter, a XbaI/NcoI fragment 5' to the *Brassica napus* ALS3 structural gene (or a nucleotide sequence that has substantial sequence similarity to said XbaI/NcoI fragment), represents a particularly useful constitutive promoter (see, PCT publication WO 96/30530).

(C) Tissue-Specific or Tissue-Preferred Promoters.

In still other embodiments, a tissue-specific promoter is operably linked to a gene for expression in tobacco. Optionally, the tissue-specific promoter is operably linked to a nucleotide sequence encoding a signal sequence which is operably linked to a gene for expression in tobacco. Plants transformed with a gene of interest operably linked to a tissue-specific promoter produce the protein product of the transgene exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai et al., (1983) *Science* 23: 476 and Sengupta-Gopalan et al., (1985) *Proc. Natl. Acad. Sci. USA* 82: 3320); a leaf-specific and light-induced promoter such as that from cab or rubisco (Simpson et al., (1985) *EMBO J.* 4: 2723 and Timko et al., (1985) *Nature* 318: 579); an anther-specific promoter such as that from LAT52 (Twell et al., (1989) *Mol. Gen. Genet.* 217: 240); a pollen-specific promoter such as that from Zm13 (Guerrero et al., (1993) *Mol. Gen. Genet* 224: 161) or a microspore-preferred promoter such as that from apg (Twell et al., (1993) *Sex. Plant Reprod.* 6: 217).

3. Signal Sequences for Targeting Proteins to Subcellular Compartments.

Transport of proteins produced by transgenes to a subcellular compartment such as the chloroplast, vacuole, peroxisome, glyoxysome, cell wall or mitochondrion, or for secretion into the apoplast, may be accomplished by means of operably linking the nucleotide sequence encoding a signal sequence typically at the 5' and/or 3' region of a gene encoding the protein of interest. Association of targeting sequences with the structural gene may determine, during protein synthesis and processing, where the encoded protein is ultimately compartmentalized. The presence of a signal sequence directs a polypeptide to either an intracellular organelle or subcellular compartment or for secretion to the apoplast. Many signal sequences are known in the art (see, for example, Becker et al., (1992) *Plant Mol. Biol.* 20: 49; Close, P. S., Master's Thesis, Iowa State University (1993); Knox, C., et al., (1987) *Plant Mol. Biol.* 9: 3; Lerner et al., (1989) *Plant Physiol.* 91: 124; Fontes et al., (1991) *Plant Cell* 3: 483; Matsuoka et al., (1991) *Proc. Natl. Acad. Sci.* 88: 834; Gould et al., (1989) *J. Cell Biol* 108: 1657; Creissen et al., (1991) *Plant J.* 2: 129; Kalderon et al., (1984) *Cell* 39: 499; Stiefel et al., (1990) *Plant Cell* 2: 785).

B. Foreign Genes that may be Introduced into Tobacco Plants.

With transgenic plants according to the present invention, a foreign protein can be produced in commercial quantities. Thus, techniques for the selection and propagation of transformed plants, which are well understood in the art, yield a plurality of transgenic plants, which are harvested in a conventional manner, and a foreign protein can then be extracted from a tissue of interest or from total biomass. Protein extraction from plant biomass can be accomplished by known methods which are discussed, for example, by Heney and Orr, (1991) *Anal. Biochem.* 114: 92.

According to a preferred embodiment, the transgenic tobacco plant is provided for commercial production of foreign protein. A genetic map can be generated, for example, via conventional Restriction Fragment Length Polymorphisms (RFLP), Polymerase Chain Reaction (PCR) analysis, and Simple Sequence Repeats (SSR), which identifies the approximate chromosomal location of the integrated DNA molecule. For exemplary methodologies in this regard, see Glick and Thompson, METHODS IN PLANT MOLECULAR BIOLOGY AND BIOTECHNOLOGY 269–284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, genes of agronomic importance can be expressed in transformed plants. More particularly, plants can be genetically engineered to express various phenotypes of agronomic interest. Exemplary genes implicated in this regard include, but are not limited to, those described below.

For example, a trait transferred into cultivar NC 2000 may confer resistance to brown stem rot (U.S. Pat. No. 5,689, 035) or resistance to cyst nematodes (U.S. Pat. No. 5,491, 081). In a preferred embodiment, a transgene whose expression results or contributes to a desired trait to be transferred to cultivar NC 2000 comprises a gene encoding an insecticidal protein, such as, for example, a crystal protein of *Bacillus thuringiensis* or a vegetative insecticidal protein from *Bacillus cereus*, such as VIP3 (see, for example, Estruch et al. (1997) *Nat Biotechnol* 15:137). In another preferred embodiment, a transgene introduced into cultivar NC 2000 comprises a herbicide tolerance gene whose expression renders plants of cultivar NC 2000 tolerant to the herbicide. For example, expression of an altered acetohydroxyacid synthase (AHAS) enzyme confers upon plants tolerance to various imidazolinone or sulfonamide herbicides (U.S. Pat. No. 4,761,373). In another preferred embodiment, a gene conferring tolerance to imidazolinones or sulfonylurea herbicides is transferred into cultivar NC 2000. Expression of a mutant acetolactate synthase (ALS) will render the plants resistant to inhibition by sulfonylurea herbicides (U.S. Pat. No. 5,013,659). In another preferred embodiment, U.S. Pat. No. 4,975,374, relates to plant cells and plants containing a gene encoding a mutant glutamine synthetase (GS) resistant to inhibition by herbicides that are known to inhibit GS, e.g., phosphinothricin and methionine sulfoximine. In addition, expression of a Streptomyces bar gene encoding a phosphinothricin acetyl transferase results in tolerance to the herbicide phosphinothricin or glufosinate (U.S. Pat. No. 5,489,520). U.S. Pat. No. 5,162,602 discloses plants tolerant to inhibition by cyclohexanedione and aryloxyphenoxypropanoic acid herbicides. The tolerance is conferred by an altered acetyl coenzyme A carboxylase (ACCase). U.S. Pat. No. 5,554,798 discloses transgenic glyphosate tolerant plants, which tolerance is conferred by an altered 5-enolpyruvyl-3-phosphoshikimate (EPSP) synthase gene. In another particular embodiment, tolerance to a protoporphyrinogen oxidase inhibitor is achieved by expression of a tolerant protoporphyrinogen oxidase enzyme in plants (U.S. Pat. No. 5,767,373). In another particular embodiment, a nucleic acid transferred into cultivar NC 2000 comprises a transgene conferring tolerance to a herbicide and at least one other transgene conferring another trait, such as for example, insect resistance or tolerance to another herbicide.

Other illustrative transgenes are set forth below.

1. Genes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with a cloned resistance gene to engineer plants that are resistant to specific pathogen strains (see, for example, Jones et al., (1994) *Science* 266: 789, cloning of the tomato Cf-9 gene for resistance to *Cladosporium fulvum*; Martin et al., (1993) *Science* 262: 1432, tomato Pto gene for resistance to *Pseudomonas syringae* pv.; Mindrinos et al., (1994) *Cell* 78: 1089, *Arabidopsis* RSP2 gene for resistance to *Pseudomonas syringae*).

(B) A *Bacillus thuringiensis* protein, a derivative thereof or a synthetic polypeptide modeled thereon (see, for example, Geiser et al., (1986) *Gene* 48: 109, disclosing the cloning and nucleotide sequence of a Bt δ-endotoxin gene). Moreover, DNA molecules encoding δ-endotoxin genes can be purchased from American Type Culture Collection (Rockville, Md.), for example, under ATCC Accession Nos. 40098, 67136, 31995 and 31998.

(C) A lectin (see, for example, the disclosure by Van Damme et al., (1994) *Plant Molec. Biol.* 24: 25), which discloses the nucleotide sequences of several *Clivia miniata* mannose-binding lectin genes.

(D) A vitamin-binding protein such as avidin (see PCT publication WO 93/06487). This publication teaches the use of avidin and avidin homologues as larvicides against insect pests.

(E) An enzyme inhibitor, for example, a protease inhibitor or an amylase inhibitor (see, for example, Abe et al., (1987) *J. Biol. Chem.* 262: 16793, nucleotide sequence of rice cysteine proteinase inhibitor; Huub et al., (1993) *Plant Molec. Biol.* 21: 985; nucleotide sequence of cDNA encoding tobacco proteinase inhibitor 1; and Sumitani et al., (1993) *Biosci. Biotech. Biochem.* 57: 1243, nucleotide sequence of *Streptomyces nitrosporeus* amylase inhibitor).

(F) An insect-specific hormone or pheromone such as an ecdysteroid or juvenile hormone, a variant thereof, a mimetic based thereon, or an antagonist or agonist thereof (see, for example, the disclosure of Hammock et al., (1990) *Nature* 344: 458, of baculovirus expression of cloned juvenile hormone esterase, an inactivator of juvenile hormone).

(G) An insect-specific peptide or neuropeptide which, upon expression, disrupts the physiology of the affected pest (for example, see the disclosures of Regan, (1994) *J. Biol. Chem.* 269: 9, expression cloning yields DNA coding for insect diuretic hormone receptor; Pratt et al., (1989) *Biochem. Biophys. Res. Comm.* 163: 1243, an allostatin is identified in *Diploptera puntata*). See also U.S. Pat. No. 5,266,317 to Tomalski et al., which discloses genes encoding insect-specific, paralytic neurotoxins.

(H) An insect-specific venom produced in nature by a snake, a wasp, or the like (see, e.g., Pang et al., (1992) *Gene* 116: 165, for disclosure of heterologous expression in plants of a gene coding for a scorpion insectotoxic peptide).

(I) An enzyme responsible for an hyperaccumulation of a monterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic (see PCT application WO 93/02197 in the name of Scott et al., which discloses the nucleotide sequence of a callase gene). DNA molecules which contain chitinase-encoding sequences can be obtained, for example, from the ATCC under Accession Nos. 39637 and 67152 (see also Kramer et al., (1993) *Insect Biochem. Molec. Biol.* 23: 691, which describes the nucleotide sequence of a cDNA encoding tobacco hookworm chitinase, and Kawalleck et al., (1993) *Plant Molec. Biol.* 21: 673, which provides the nucleotide sequence of the parsley ubi4-2 polyubiquitin gene).

(K) A molecule that stimulates signal transduction. For example, see the disclosure by Botella et al., (1994) *Plant Molec. Biol.* 24: 757, of nucleotide sequences for mung bean calmodulin cDNA clones, and Griess et al., (1994) *Plant Physio.* 104: 1467, which provides the nucleotide sequence of a maize calmodulin cDNA clone.

(L) A hydrophobic moment peptide (see PCT application WO 95/16776 which disclosures peptide derivatives of Tachyplesin which inhibit fungal plant pathogens, and PCT application WO 95/18855 which teaches synthetic antimicrobial peptides that confer disease resistance).

(M) A membrane permease, a channel former or a channel blocker. For example, see the disclosure by Jaynes et al., (1993) *Plant Sci.* 89: 43), of heterologous expression of a cecropin-βlytic peptide analog to render transgenic tobacco plants resistant to *Pseudomonas solanacearum*.

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses (see Beachy et al., (1990) *Ann. Rev. Phytopathol.* 28: 451). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus (Id.).

(O) An insect-specific antibody or an immunotoxin derived therefrom. Thus, an antibody targeted to a critical metabolic function in the insect gut would inactivate an affected enzyme, killing the insect (Cf. Taylor et al., Abstract #497, SEVENTH INT'L SYMPOSIUM ON MOLECULAR PLANT-MICROBE INTERACTIONS (Edinburgh, Scotland, 1994; enzymatic inactivation in transgenic tobacco via production of single-chain antibody fragments).

(P) A virus-specific antibody (see, for example, Taviadoraki et al., (1993) *Nature* 366: 469; showing that transgenic plants expressing recombinant antibody genes are protected from virus attack).

(Q) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase (see Lamb et al., (1992) *Bio/Technology* 10: 1436). The cloning and characterization of a gene which encodes a bean endopolygalacturonase-inhibiting protein is described by Toubart et al., (1992) *Plant J.* 2: 367.

(R) A developmental-arrestive protein produced in nature by a plant. For example, Logemann et al., (1992) *Bio/Technology* 10: 305, have shown that transgenic plants expressing the barley ribosome-inactivating gene have an increased resistance to fungal disease.

2. Genes that Confer Resistance to a Herbicide, for Example:

(A) An herbicide that inhibits the growing point or meristem, such as an imidazalinone or a sulfonylurea. Exemplary genes in this category code for mutant ALS or AHAS enzyme as described, for example, by Lee et al., (1988) *EMBO J.* 7: 1241, and Miki et al., (1990) *Theor. Appl. Genet* 80: 449, respectively.

(B) Glyphosate (resistance imparted by mutant 5-enolpyruvl-3-phosphikimate synthase (EPSP) and aroA genes) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., (1989) *Bio/Technology* 7: 61, describe the production of transgenic plants that express chimeric bar genes coding for phosphinothricin acetyl transferase activity. Exemplary of genes conferring resistance to phenoxy proprionic acids and cycloshexones, such as sethoxydim and haloxyfop, are the Acc1-S1, Acc1-S2 and Acc1-S3 genes described by Marshall et al., (1992) *Theor. Appl. Genet.* 83: 435.

(C) An herbicide that inhibits photosynthesis, such as a triazine (psbA and gs+ genes) and a benzonitrile (nitrilase gene). Przbilla et al., (1991) *Plant Cell* 3: 169, describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., (1992) *Biochem. J.* 285: 173.

3. Genes that Confer or Contribute to a Value-Added Trait, Such as:

(A) Altered chemical composition, for example, an increase or decrease in nicotine, total alkaloid, or reducing sugar content.

(B) Decreased phytate content:
(i) Introduction of a phytase-encoding gene would enhance breakdown of phytate, adding more free phosphate to the transformed plant. For example, see Van Hartingsveldt et al., (1993) *Gene* 127: 87, for a disclosure of the nucleotide sequence of an *Aspergillus niger* phytase gene.

(C) Modified carbohydrate composition effected, for example, by transforming plants with a gene coding for an enzyme that alters the branching pattern of starch (see Shiroza et al., (1998) *J. Bacteriol.* 170: 810, nucleotide sequence of *Streptococcus mutans* fructosyltransferase gene; Steinmetz et al., (1985) *Mol. Gen. Genet.* 200: 220, nucleotide sequence of *Bacillus subtilis* levansucrase gene; Pen et al., (1992) *Bio/Technology* 10: 292, production of transgenic plants that express *Bacillus licheniformis* α-amylase; Elliot et al., (1993) *Plant Molec. Biol.* 21: 515, nucleotide sequences of tomato invertase genes; Søgaard et al., (1993) *J. Biol. Chem.* 268: 22480, site-directed mutagenesis of barley α-amylase gene; and Fisher et al., (1993) *Plant Physiol.* 102: 1045, maize endosperm starch branching enzyme II).

Those skilled in the art will appreciate that the transgenes described above may also be transferred into tobacco plants using conventional breeding techniques as known in the art and as described herein.

As a further alternative, the transgene encodes an antisense RNA molecule or any other non-translated RNA as known in the art. In a further alternative embodiment, the transgene effects gene suppression in the host plant.

C. Methods for Tobacco Transformation.

Plants can be transformed according to the present invention using any suitable method known in the art. Intact plants, plant tissue, explants, meristematic tissue, protoplasts, callus tissue, cultured cells, and the like may be used for transformation depending on the plant species and the method employed. In a preferred embodiment, intact plants are inoculated using microprojectiles carrying a nucleic acid to be transferred into the plant. The site of inoculation will be apparent to one skilled in the art; leaf tissue is one example of a suitable site of inoculation. In preferred embodiments, intact plant tissues or plants are inoculated, without the need for regeneration of plants (e.g., from callus).

Exemplary transformation methods include biological methods using viruses and *Agrobacterium*, physicochemical methods such as electroporation, polyethylene glycol, ballistic bombardment, microinjection, and the like.

In one form of direct transformation, the vector is microinjected directly into plant cells by use of micropipettes to mechanically transfer the recombinant DNA (Crossway, *Mol. Gen. Genetics* 202: 179 (1985)).

In another protocol, the genetic material is transferred into the plant cell using polyethylene glycol (Krens, et al. *Nature* 296, 72 (1982)).

In still another method, protoplasts are fused with minicells, cells, lysosomes, or other fusible lipid-surfaced bodies that contain the nucleotide sequence to be transferred to the plant (Fraley, et al., *Proc. Natl. Acad. Sci. USA* 79, 1859 (1982)).

DNA may also be introduced into the plant cells by electroporation (Fromm et al., *Proc. Natl. Acad. Sci. USA* 82, 5824 (1985)). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide and regenerate. One advantage of electroporation is that large pieces of DNA, including artificial chromosomes, can be transformed by this method.

Viruses include RNA and DNA viruses (e.g., geminiviruses, badnaviruses, nanoviruses and caulimoviruses).

Ballistic transformation typically comprises the steps of: (a) providing a plant tissue as a target; (b) propelling a microprojectile carrying the heterologous nucleotide sequence at the plant tissue at a velocity sufficient to pierce the walls of the cells within the tissue and to deposit the nucleotide sequence within a cell of the tissue to thereby provide a transformed tissue. In particular preferred embodiments of the invention, the method further includes the step of culturing the transformed tissue with a selection agent. In particular embodiments, the selection step is followed by the step of regenerating transformed plants from the transformed tissue. As noted below, the technique may be carried out with the nucleotide sequence as a precipitate (wet or freeze-dried) alone, in place of the aqueous solution containing the nucleotide sequence.

Any ballistic cell transformation apparatus can be used in practicing the present invention. Exemplary apparatus are disclosed by Sandford et al. (*Particulate Science and Technology* 5, 27 (1988)), Klein et al. (*Nature* 327, 70 (1987)), and in EP 0 270 356. Such apparatus have been used to transform maize cells (Klein et al., *Proc. Natl. Acad. Sci. USA* 85, 4305 (1988)), soybean callus (Christou et al., *Plant Physiol.* 87, 671 (1988)), McCabe et al., *BioTechnology* 6, 923 (1988), yeast mitochondria (Johnston et al., *Science* 240, 1538 (1988)), and *Chlamydomonas* chloroplasts (Boynton et al., *Science* 240, 1534 (1988)).

Alternately, an apparatus configured as described by Klein et al. (*Nature* 70, 327 (1987)) may be utilized. This apparatus comprises a bombardment chamber, which is divided into two separate compartments by an adjustable-height stopping plate. An acceleration tube is mounted on top of the bombardment chamber. A macroprojectile is propelled down the acceleration tube at the stopping plate by a gunpowder charge. The stopping plate has a borehole formed therein, which is smaller in diameter than the microprojectile. The macroprojectile carries the microprojectile(s), and the macroprojectile is aimed and fired at the borehole. When the macroprojectile is stopped by the stopping plate, the microprojectile(s) is propelled through the borehole. The target tissue is positioned in the bombardment chamber so that a microprojectile(s) propelled through the bore hole penetrates the cell walls of the cells in the target tissue and deposit the nucleotide sequence of interest carried thereon in the cells of the target tissue. The bombardment chamber is partially evacuated prior to use to prevent atmospheric drag from unduly slowing the microprojectiles. The chamber is only partially evacuated so that the target tissue is not desiccated during bombardment. A vacuum of between about 400 to about 800 millimeters of mercury is suitable.

In alternate embodiments, ballistic transformation is achieved without use of microprojectiles. For example, an aqueous solution containing the nucleotide sequence of interest as a precipitate may be carried by the macroprojectile (e.g., by placing the aqueous solution directly on the plate-contact end of the macroprojectile without a microprojectile, where it is held by surface tension), and the solution alone propelled at the plant tissue target (e.g., by propelling the macroprojectile down the acceleration tube in the same manner as described above). Other approaches include placing the nucleic acid precipitate itself ("wet" precipitate) or a freeze-dried nucleotide precipitate directly on the plate-contact end of the macroprojectile without a microprojectile. In the absence of a microprojectile, it is believed that the nucleotide sequence must either be propelled at the tissue target at a greater velocity than that needed if carried by a microprojectile, or the nucleotide sequenced caused to travel a shorter distance to the target tissue (or both).

It is currently preferred to carry the nucleotide sequence on a microprojectile. The microprojectile may be formed from any material having sufficient density and cohesiveness to be propelled through the cell wall, given the particle's velocity and the distance the particle must travel. Non-limiting examples of materials for making microprojectiles include metal, glass, silica, ice, polyethylene, polypropylene, polycarbonate, and carbon compounds (e.g., graphite, diamond). Metallic particles are currently preferred. Non-limiting examples of suitable metals include tungsten, gold, and iridium. The particles should be of a size sufficiently small to avoid excessive disruption of the cells they contact in the target tissue, and sufficiently large to provide the inertia required to penetrate to the cell of interest in the target tissue. Particles ranging in diameter from about one-half micrometer to about three micrometers are suitable. Particles need not be spherical, as surface irregularities on the particles may enhance their DNA carrying capacity.

The nucleotide sequence may be immobilized on the particle by precipitation. The precise precipitation parameters employed will vary depending upon factors such as the particle acceleration procedure employed, as is known in the art. The carrier particles may optionally be coated with an encapsulating agents such as polylysine to improve the stability of nucleotide sequences immobilized thereon, as discussed in EP 0 270 356 (column 8).

Alternatively, plants may be transformed using *Agrobacterium tumefaciens* or *Agrobacterium rhizogenes*, preferably *Agrobacterium tumefaciens*. *Agrobacterium*-mediated gene transfer exploits the natural ability of *A. tumefaciens* and *A. rhizogenes* to transfer DNA into plant chromosomes. *Agrobacterium* is a plant pathogen that transfers a set of genes encoded in a region called T-DNA of the Ti and Ri plasmids of *A. tumefaciens* and *A. rhizogenes*, respectively, into plant cells. The typical result of transfer of the Ti plasmid is a tumorous growth called a crown gall in which the T-DNA is stably integrated into a host chromosome. Integration of the Ri plasmid into the host chromosomal DNA results in a condition known as "hairy root disease". The ability to cause disease in the host plant can be avoided by deletion of the genes in the T-DNA without loss of DNA transfer and integration. The DNA to be transferred is attached to border sequences that define the end points of an integrated T-DNA.

Gene transfer by means of engineered *Agrobacterium* strains has become routine for many dicotyledonous plants. Some difficulty has been experienced, however, in using *Agrobacterium* to transform monocotyledonous plants, in particular, cereal plants. However, *Agrobacterium* mediated transformation has been achieved in several monocot species, including cereal species such as rye (de la Pena et al., *Nature* 325, 274 (1987)), maize (Rhodes et al., *Science* 240, 204 (1988)), and rice (Shimamoto et al., *Nature* 338, 274 (1989)).

While the following discussion will focus on using *A. tumefaciens* to achieve gene transfer in plants, those skilled in the art will appreciate that this discussion also applies to *A. rhizogenes*. Transformation using *A. rhizogenes* has developed analogously to that of *A. tumefaciens* and has been successfully utilized to transform, for example, alfalfa, *Solanum nigrum* L., and poplar. U.S. Pat. No. 5,777,200 to Ryals et al. As described by U.S. Pat. No. 5,773,693 to Burgess et al., it is preferable to use a disarmed *A. tumefaciens* strain (as described below), however, the wild-type *A. rhizogenes* may be employed. An illustrative strain of *A. rhizogenes* is strain 15834.

The *Agrobacterium* strain is typically modified to contain the nucleotide sequences to be transferred to the plant. The nucleotide sequence to be transferred is incorporated into the T-region and is typically flanked by at least one T-DNA border sequence, preferably two T-DNA border sequences. A variety of *Agrobacterium* strains are known in the art, and can be used in the methods of the invention. See, e.g., Hooykaas, *Plant Mol. Biol.* 13, 327 (1989); Smith et al., *Crop Science* 35, 301 (1995); Chilton, *Proc. Natl. Acad. Sci. USA* 90, 3119 (1993); Mollony et al., *Monograph Theor. Appl. Genet NY* 19, 148 (1993); Ishida et al., *Nature Biotechnol.* 14, 745 (1996); and Komari et al., *The Plant Journal* 10, 165 (1996).

In addition to the T-region, the Ti (or Ri) plasmid contains a vir region. The vir region is important for efficient transformation, and appears to be species-specific.

Two exemplary classes of recombinant Ti and Ri plasmid vector systems are commonly used in the art. In one class, called "cointegrate," the shuttle vector containing the gene of interest is inserted by genetic recombination into a non-oncogenic Ti plasmid that contains both the cis-acting and trans-acting elements required for plant transformation as, for example, in the PMLJ1 shuttle vector of DeBlock et al., *EMBO J.* 3, 1681 (1984), and the non-oncogenic Ti plasmid pGV2850 described by Zambryski et al., *EMBO J.* 2, 2143 (1983). In the second class or "binary" system, the gene of interest is inserted into a shuttle vector containing the cis-acting elements required for plant transformation. The other necessary functions are provided in trans by the non-oncogenic Ti plasmid as exemplified by the pBIN19 shuttle vector described by Bevan, *Nucleic Acids Research* 12, 8711 (1984), and the non-oncogenic Ti plasmid PAL4404 described by Hoekma, et al., *Nature* 303, 179 (1983).

Binary vector systems have been developed where the manipulated disarmed T-DNA carrying the heterologous nucleotide sequence of interest and the vir functions are present on separate plasmids. In this manner, a modified T-DNA region comprising foreign DNA (the nucleic acid to be transferred) is constructed in a small plasmid that replicates in *E. coli*. This plasmid is transferred conjugatively in a tri-parental mating or via electroporation into *A. tumefaciens* that contains a compatible plasmid with virulence gene sequences. The vir functions are supplied in trans to transfer the T-DNA into the plant genome. Such binary vectors are useful in the practice of the present invention.

In particular embodiments of the invention, super-binary vectors are employed. See, e.g., U.S. Pat. No. 5,591,615 and EP 0 604 662. Such a super-binary vector has been constructed containing a DNA region originating from the hypervirulence region of the Ti plasmid pTiBo542 (Jin et al., *J. Bacteriol.* 169, 4417 (1987)) contained in a super-virulent *A. tumefaciens* A281 exhibiting extremely high transformation efficiency (Hood et al., *Biotechnol.* 2, 702 (1984); Hood et al., *J. Bacteriol.* 168, 1283 (1986); Komari et al., *J. Bacteriol.* 166, 88 (1986); Jin et al., *J. Bacteriol.* 169, 4417 (1987); Komari, *Plant Science* 60, 223 (1987); ATCC Accession No. 37394.

Exemplary super-binary vectors known to those skilled in the art include pTOK162 (Japanese patent Appl. (Kokai) No. 4-222527, EP 504,869, EP 604,662, and U.S. Pat. No. 5,591,616) and pTOK233 (Komari, *Plant Cell Reports* 9, 303 (1990); Ishida et al., *Nature Biotechnology* 14, 745 (1996)). Other super-binary vectors may be constructed by the methods set forth in the above references. Super-binary vector pTOK162 is capable of replication in both *E. coli* and in *A. tumefaciens*. Additionally, the vector contains the virB, virC and virG genes from the virulence region of pTiBo542. The plasmid also contains an antibiotic resistance gene, a selectable marker gene, and the nucleic acid of interest to be transformed into the plant. The nucleic acid to be inserted into the plant genome is typically located between the two border sequences of the T region. Super-binary vectors can be constructed having the features described above for pTOK162. The T-region of the super-binary vectors and other vectors for use in the invention are constructed to have restriction sites for the insertion of the genes to be delivered. Alternatively, the DNA to be transformed can be inserted in the T-DNA region of the vector by utilizing in vivo homologous recombination. See, Herrera-Esterella et al., *EMBO J.* 2, 987 (1983); Horch et al., *Science* 223, 496 (1984). Such homologous recombination relies on the fact that the super-binary vector has a region homologous with a region of pBR322 or other similar plasmids. Thus, when the two plasmids are brought together, a desired gene is inserted into the super-binary vector by genetic recombination via the homologous regions.

Plant cells may be transformed with Agrobacteria by any means known in the art, e.g., by co-cultivation with cultured isolated protoplasts, or transformation of intact cells or tissues. The first requires an established culture system that allows for culturing protoplasts and subsequent plant regeneration from cultured protoplasts. Identification of transformed cells or plants is generally accomplished by including a selectable marker in the transforming vector, or by obtaining evidence of successful bacterial infection.

In plants stably transformed by Agrobacteria-mediated transformation, the nucleotide sequence of interest is incorporated into the plant genome, typically flanked by at least one T-DNA border sequence. Preferably, the nucleotide sequence of interest is flanked by two T-DNA border sequences.

Plant cells, which have been transformed by any method known in the art, can also be regenerated to produce intact plants using known techniques.

Plant regeneration from cultured protoplasts is described in Evans et al., *Handbook of Plant Cell Cultures*, Vol. 1: (MacMilan Publishing Co. New York, 1983); and Vasil I. R. (ed.), *Cell Culture and Somatic Cell Genetics of Plants*, Acad. Press, Orlando, Vol. I, 1984, and Vol. II, 1986). It is known that practically all plants can be regenerated from cultured cells or tissues, including but not limited to, all major species of sugar-cane, sugar beet, cotton, fruit trees, and legumes.

Means for regeneration vary from species to species of plants, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. It is also advantageous to add glutamic acid and proline to the medium, especially for such species as corn and alfalfa. Efficient regeneration will depend on the medium, on the genotype, and on the history of the culture. If these three variables are controlled, then regeneration is usually reproducible and repeatable.

A large number of plants have been shown capable of regeneration from transformed individual cells to obtain transgenic whole plants.

The regenerated plants are transferred to standard soil conditions and cultivated in a conventional manner. The plants are grown and harvested using conventional procedures.

The particular conditions for transformation, selection and regeneration may be optimized by those of skill in the art. Factors that affect the efficiency of transformation include the species of plant, the tissue infected, composition of the media for tissue culture, selectable marker genes, the length of any of the above-described step, kinds of vectors, and light/dark conditions. Therefore, these and other factors may be varied to determine what is an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

The foregoing methods for transformation may be used for producing transgenic inbred or doubled-haploid lines. Transgenic inbred/doubled-haploid lines could then be crossed, with another (non-transformed or transformed) inbred or doubled-haploid line, in order to produce a transgenic hybrid tobacco plant. Alternatively, a genetic trait which has been engineered into a particular tobacco line using the foregoing transformation techniques could be moved into another line using traditional backcrossing techniques that are well known in the plant breeding arts. For example, a backcrossing approach could be used to move an engineered trait from a non-elite line into an elite tobacco line, or from a hybrid tobacco plant containing a foreign gene in its genome into a line or lines which do not contain that gene. As used above, "crossing" can refer to a simple X by Y cross, or the process of backcrossing, depending on the context.

VI. Industrial Applicability

This invention is also directed to methods for producing a tobacco plant by crossing a first parent tobacco plant with a second parent tobacco plant wherein either the first or second parent tobacco plant is a tobacco plant of cultivar NC 2000 or a tobacco plant of cultivar NC 2000 further comprising one or more additional traits (e.g., single gene traits). Further, both first and second parent tobacco plants can come from cultivar NC 2000 or a tobacco plant of cultivar NC 2000 further comprising one or more traits (e.g., single gene traits). Thus, any such methods using the tobacco cultivar NC 2000 or a tobacco plant of NC 2000 further comprising one or more additional traits (e.g., one or more single gene traits) are part of this invention: selfing, backcrosses, doubled-haploid production, hybrid production, crosses to populations, and the like. All plants produced using tobacco cultivar NC 2000 or modified cultivar NC 2000 further comprising one or more additional traits (e.g., one or more single gene traits) as a parent are within the scope of this invention. Advantageously, tobacco cultivar NC 2000 or modified cultivar NC 2000 further comprising one or more additional traits (e.g., one or more single gene traits) are used in crosses with other, different, tobacco inbreds or doubled-haploids to produce first generation ($F_1$) tobacco hybrid seeds and plants with superior characteristics.

As used herein, the term "plant" includes plant cells, plant protoplasts and plant tissue cultures from which tobacco plants can be regenerated, plant calli, plant clumps, and plant cells that are intact in plants or parts of plants, such as leaves, pollen, embryos, cotyledon, hypocotyl, roots, root tips, anthers, flowers and parts thereof, ovules, shoots, stems, stalks, pith, capsules, and the like.

As used herein, the term "tissue culture" encompasses cultures of tobacco tissue, cells, protoplasts and callus. Methods of culturing tobacco tissue, cells, protoplasts and callus, as well as methods of regenerating plants from tobacco tissue cultures are described in Wernsman, E. A., and Rufty, R. C. 1987. Chapter Seventeen. Tobacco. Pages 669–698 In: Cultivar Development. Crop Species. W. H. Fehr (ed.), MacMillan Publishing Go., Inc., New York, N.Y. 761 pp. Thus, another aspect of this invention is to provide cells which upon growth and differentiation produce tobacco plants having the physiological and morphological characteristics of tobacco cultivar NC 2000. In a preferred embodiment, cells of cultivar NC 2000 are transformed genetically, for example with one or more genes described above, and transgenic plants of tobacco cultivar NC 2000 are regenerated therefrom.

VII. Deposits.

A deposit of at least 2500 seeds of tobacco cultivar NC 2000 has been deposited with the American Type Culture Collection (ATCC), Manassas, Va. 20110 USA on Sep. 21, 2001. The deposit has been assigned ATCC Accession Number PTA-3721. This deposit of the tobacco cultivar NC 2000 will be maintained in the ATCC depository, which is a public depository, for a period of 30 years, or 5 years after the most recent request, or for the effective life of the patent, whichever is longer, and will be replaced if it becomes nonviable during that period.

Having now described the invention, the same will be illustrated with reference to certain examples, which are included herein for illustration purposes only, and which are not intended to be limiting of the invention.

EXAMPLE 1

To the inventor's knowledge, NC 2000 is most similar to one of its parents, KY 14; however, NC 2000 is highly resistant to blue mold caused by the fungal pathogen *Peronospora tabacina* Adam (see Table 3), whereas KY 14 is susceptible.

The NC BMR-113 parent also exhibits resistance to blue mold. However, NC 2000 is a cultivar, whereas NC BMR-113 is a germplasm line that is not adapted or suitable for commercial cultivation.

Blue Mold Resistance:

Field evaluations of blue mold resistance in NC 2000 and check cultivars were conducted at the Mountain Research Station in Waynesville, N.C. and at the Upper Mountain Research Station in Laurel Springs, N.C. in years 1995–1998. NC 2000 was entered into the Regional Burley Variety Evaluation Test in 1998. In addition to evaluations conducted in the burley growing belt, evaluations for blue mold reaction were also performed under natural epidemics in Papantla, Veracruz, Mexico.

Blue mold resistance in NC 2000 is manifested by reduced number and size of lesions with minimum sporulation. Based on the studies at the two North Carolina research stations, NC 2000 is resistant against multiple isolates of the blue mold fungus, including Metaxyl-sensitive and Metaxyl-resistant strains. Tables 1 through 4, below, were compiled from data obtained from the 1998 Regional Burley Variety Evaluation Test, and from experiments conducted at the Mountain and Upper Mountain Research Stations and Papantla, Veracruz, Mexico from 1995–1998. Table 3 presents data related to percent leaf area damaged due to blue mold for cultivars NC 2000, KY 14, TN 86 and OVENS 62 (a flue-cured blue mold resistant cultivar). A score was given to each plot according to the percentage of the leaf area damaged (% LAD), and then that score was transformed into a geometric mean (Horsfall and Barrett, (1945) *Phytopathology* 36:655).

Other Characteristics:

Similar to KY 14, NC 2000 is also resistant to tobacco mosaic virus (TMV) and wildfire (*Pseudomonas syringae* pv. *tabaci*), and is susceptible to black shank (races 1 and 0), black root rot, and the polyvirus complex (see Table 4). Leaf yield of NC 2000 is similar to KY 14 (see, Tables 1 and 2).

Tobacco cultivar NC 2000 also differs from KY 14 in the following respects:

Time to maturity for NC 2000 is approximately nine days later than for KY 14.

NC 2000 is approximately 12 centimeters shorter than KY 14 (topped) and approximately 13 centimeters shorter than KY 14 (not topped).

The leaves of NC 2000 are approximately 1 to 9 cm shorter and 1 to 2.5 centimeters narrower than those of KY 14.

TABLE 1

Mean yield (lbs/acre), grade index and chemical composition of check cultivars and NC 2000 in the 1998 Regional Small Plot tests grown at seven locations.

| Variety | Yield lbs./A | Grade Index | Nicotine % |
|---|---|---|---|
| KY 14 | 2623 | 69 | 4.10 |
| VA 509 | 2638 | 72 | 4.73 |
| NC 2000 | 2348 | 69 | 4.95 |

TABLE 2

Mean yield (lbs/acre), grade index and chemical composition of check cultivars and NC 2000 grown at the Upper Mountain Research Station (UMRS), Laurel Springs, NC and the Mountain Research Station (MRS), Waynesville, NC in 1995, 1996, 1997, and 1998.

| Variety | UMRS Yield lbs./A | MRS Yield lbs./A | Mean Yield lbs./A | Grade Index | Total Alkaloids |
|---|---|---|---|---|---|
| 1995 | | | | | |
| KY 14 | 2785 | 2036 | 2411 | 71 | 3.78 |
| TN 86 | 2944 | 2358 | 2651 | 71 | 3.32 |
| NC 2000 | 2658 | 2282 | 2470 | 69 | 2.75 |
| 1996 | | | | | |
| KY 14 | 2105 | 1048 | 1577 | 68 | 2.54 |
| TN 86 | 2205 | 1248 | 1727 | 70 | 2.31 |
| NC 2000 | 2196 | 1114 | 1655 | 68 | 2.71 |
| 1997 | | | | | |
| KY 14 | 2127 | 1361 | 1744 | 65 | 3.58 |
| TN 86 | 2207 | 1484 | 1846 | 68 | 2.87 |
| NC 2000 | 2210 | 1155 | 1682 | 73 | 3.67 |
| 1998 | | | | | |
| KY 14 | 2005 | 2612 | 2309 | 57 | 3.63 |
| VA 509 | 2362 | 2875 | 2619 | 70 | 3.28 |
| TN 86 | 2184 | 2641 | 2413 | 64 | 2.85 |
| NC 2000 | 2476 | 2766 | 2621 | 65 | 3.28 |

TABLE 3

Evaluation of Percent Leaf Area Damaged (% LAD) due to blue mold (*Peronospora tabacina* Adam) at the Upper Mountain Research Station (UMRS), Laurel Springs, NC, the Mountain Research Station (MRS), Waynesville, NC and Papantla, Veracruz, Mexico in 1995, 1996, 1997, and 1998.

| | UMRS | MRS | MEXICO |
|---|---|---|---|
| 1995 | | | |
| KY 14 | 26.4 | — | 98.6 |
| TN 86 | 28.1 | — | 91.9 |
| OVENS 62 | 1.4 | — | 9.1 |
| NC 2000 | 12.7 | — | 15.7 |
| 1996 | | | |
| KY 14 | 35.2 | 82.6 | 66.8 |
| TN 86 | 19.2 | 28.1 | 67.2 |
| OVENS 62 | 1.4 | 1.4 | 2.1 |
| NC 2000 | 1.4 | 13.8 | 8.6 |
| 1997 | | | |
| KY 14 | 10.3 | 56.1 | 78.2 |
| TN 86 | 5.9 | 9.4 | 15.1 |
| OVENS 62 | 0.0 | 1.4 | 2.1 |
| NC 2000 | 1.4 | 1.4 | 5.3 |
| 1998 | | | |
| KY 14 | 19.7 | 3.5 | 29.5 |
| TN 86 | 8.5 | 3.3 | 19.9 |
| OVENS 62 | 0.5 | 0.2 | 1.0 |
| NC 2000 | 1.4 | 1.4 | 2.8 |

*Blue Mold disease pressure was low in the mountain regions of North Carolina in 1995 and 1998.

TABLE 4

Regional Small Plot burley tobacco disease ratings[1], 1998.

| VARIETY | BLACK SHANK | | BLACK ROOT ROT | TOBACCO MOSAIC VIRUS | TOBACCO ETCH VIRUS | WILD FIRE |
|---|---|---|---|---|---|---|
| | Race 0 | Race 1 | | | | |
| KY 14 | S | S | MS | R | S | R |
| VA 509 | MS | R | MS | S | S | R |
| NC 2000 | S | S | S | R | S | R |

[1]Disease ratings reported as R = resistant, S = susceptible, and MS = moderately susceptible.

EXAMPLE 2

Materials and Method

Identification of Markers Linked to the BMR Locus

Traditional breeding methods are difficult to use when breeding for blue mold resistance. Having to wait for natural epidemics to occur increases the interval between cycles of selection. The interaction between host and pathogen is extremely complex which causes disease reactions to be highly variable, unpredictable, and often non-reproducible. The use of molecular markers could reduce the amount of time and effort required to identify resistance in burley tobacco.

Population Development.

Two burley breeding lines released from the North Carolina Agricultural Research Service in 1992, NCBMR-113 and NCBMR-114, were used as the maternal parents and crossed with TN 90. Maternally derived doubled haploid lines were obtained through the *N. africana* method and chromosome doubled using the leaf midvein technique.

Laboratory Screening.

Fifty newly developed doubled haploid (DH) lines were screened for blue mold resistance using molecular markers found to be linked to the target gene. NCBMR-113 and NCBMR-114 and OVENS 62 were used as the resistant controls and TN 86, TN 90 and KY 14 were used as susceptible controls.

DNA Extraction.

Seed from 50 maternally-derived doubled haploid lines were sown in plastic pots on Metro-Mix 220™ (Milpitas, Calif.) growing medium. Growing conditions were kept constant at 24° C. under a 16 hour day and 9 hour night regime for approximately 8 weeks. At the 7 to 10 leaf stage tissue was taken and ground for twenty seconds with disposable pestles in 1.5 mL Eppendorf tubes. Four hundred microliters of extraction buffer (PEC: 20 mM Tris HCl, pH 7.5, 25 mM NaCl, 25 mM MEDTA, 0.5% SDS) was immediately added. Tubes were vortexed to disperse tissue evenly in solution. Samples were incubated for a minimum of ten minutes. DNA extracts were centrifuged for 1 min at 13000 rpm and 300 $\mu$l of the supernatant was transferred to a new tube along with the addition of 300 $\mu$l of isopropanol. Samples were incubated at room temperature for 2 minutes and then centrifuged for 5 minutes at 13000 rpm. Supernatant was discarded and 300 $\mu$l of 70% ethanol was added. Solution was centrifuged at 13000 rpm to form a DNA pellet, air dried and resuspended in 100 $\mu$l of TE buffer. DNA was centrifuged for 2 minutes at 10000 rpm and supernatant transferred to a new tube. Samples were stored at 4° C.

RAPD Analysis.

PCR was carried out using 10-mer primers of arbitrary sequence on a PTC-100™MJ Research Programmable Thermal Controller (MJ Research, Inc., Watertown, Mass.). Each 15 $\mu$l of master mix contained 4 $\mu$l DNA 10×PCR buffer, 200 mM dNTPS (dATP, dCTP, dGTP, dTTP), 1 unit Taq DNA Polymerase Stoffel fragment, 4 mM $MgCl_2$, 10% BSA and 20 ng primer. Gels were run in a Horizon 20–25 horizontal gel electrophoresis apparatus at 65V for a period of six hours and then visualized on an UV transilluminator.

Field Screening.

The fifty lines were evaluated in Papantla, Veracruz, Mexico for resistance to blue mold under natural conditions. Entries were replicated three times in a randomized block design. Experimental units consisted of one-row plots containing twelve plants per row. Based on the Horsfall-Barrett disease rating scale a score was given to each plot according to the percentage of the leaf area damaged (% LAD) and then that score was transformed into a geometric mean.

EXAMPLE 3

Results of Marker Analysis

Figure 2:
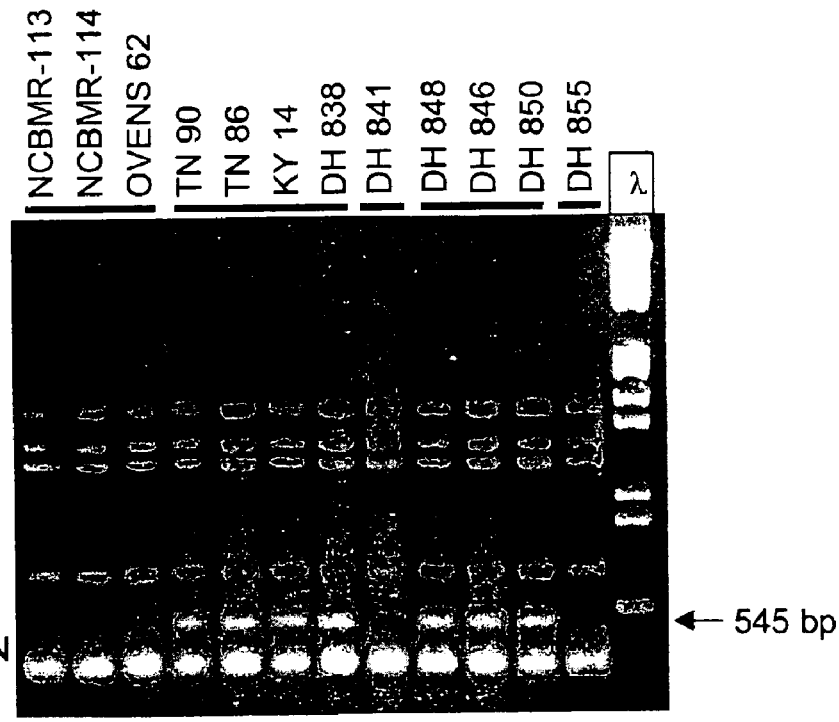

Forty primers detected polymorphic bands between the susceptible and resistant bulks, but only 21 produced bands that were linked to the gene conditioning resistance to blue mold (BMR) after individual DNA amplification of the lines comprising the bulks (Table 5). Six of these primers (UBC-149, UBC-180, UBC-534, UBC-544, UBC-610, UBC-240) were selected due to their repeatability and ease of scoring to use in pre-screening (FIGS. 1 and 2).

Figure 3:
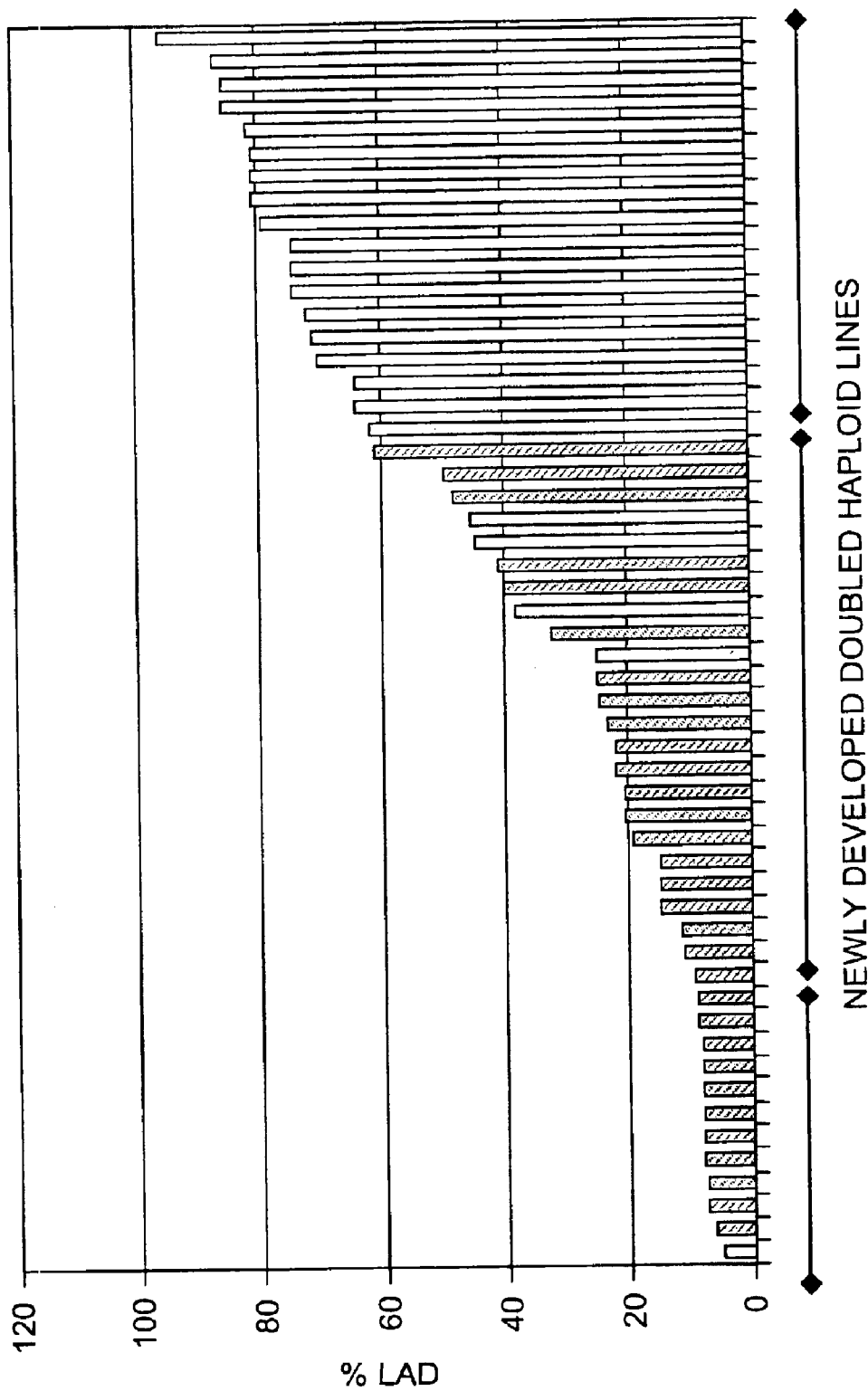
FIG. 3. The fifty doubled haploid lines showing % LAD found in field evaluations and resistant and susceptible classifications by use of markers. Higher reliability of the markers is found at the extremes of a tobacco plant's resistance or susceptibility to blue mold.

Out of the fifty newly classified DH lines, twenty-nine were classified as resistant when they were pre-screened using molecular markers. Of these twenty-nine, only fifteen had % LAD of 10% of less warranting a resistant classification in the field evaluations. Twenty-one out of the fifty DH lines were classified as susceptible using the markers. Of these twenty-nine lines, twenty were classified as susceptible in the field (FIG. 3). It is proposed that this one line that was not in agreement is a recombinant. It showed the highest level of resistance of all lines tested, including controls, in the field evaluation with a 2.3% LAD. After conducting both field and laboratory evaluations of the fifty previously unclassified doubled haploid lines it was found that the agreement between field reaction and marker classification was only 70% with reliability being higher at the extremes of resistance and susceptibility to blue mold (FIG. 3).

The investigations described in this and the previous Example are described in more detail in Milla et al. (Susana R. Milla, *Identification of RAPD Markers Linked to Blue Mold Resistance in Tobacco*, Master's Thesis, North Carolina State University, 1998).

TABLE 5

| PRIMER | Sequence 5'- to -3' | SEQ ID NO: | Type of marker | Size of frag. (bp) | Quality of amp.[a] | LINES SUSCEPTIBLE BULK | | | | | | |
|---|---|---|---|---|---|---|---|---|---|---|---|---|
| | | | | | | Ky 14 | Ky 17 | TN 86 | TN 90 | Speight G-28 | Speight G-70 | McNair 944 |
| OPAE-02 | TCGTTCACCC | 1 | coupling | 335 | *** | 0[b] | 0 | 0 | 0 | 0 | 0 | 0 |
| OPAE-07 | GTGTCAGTGG | 2 | repulsion | 316 | ** | 1 | 1 | 1 | 1 | 1 | 1 | 1 |
| OPAG-20 | TGCGCTCCTC | 3 | coupling | 416 | ** | 0 | 0 | 0 | 0 | 0 | 0 | 0 |
| OPC-09 | CTCACCGTCC | 4 | coupling | 670 | ** | 0 | 0 | 0 | 0 | 0 | 0 | 0 |
| OPP-11 | AACGCGTCGG | 5 | coupling | 663 | *** | 0 | 0 | 0 | 0 | 0 | 0 | 0 |
| OPR-06 | GTCTACCGCA | 6 | coupling | 268 | * | 0 | 0 | 0 | 0 | 0 | 0 | 0 |
| UBC-024 | ACAGGGGTGA | 7 | coupling | 589 | ** | 0 | 0 | 0 | 0 | 0 | 0 | 0 |
| UBC-149 | AGCAGCGTGG | 8 | coupling | 228 | *** | 0 | 0 | 0 | 0 | 0 | 0 | 0 |
| UBC-180 | GGGCCACGCT | 9 | coupling | 328 | ** | 0 | 0 | 0 | 0 | 0 | 0 | 0 |
| UBC-240 | ATGTTCCAGG | 10 | repulsion | 545 | ** | 1 | 1 | 1 | 1 | 1 | 1 | 1 |
| UBC-243 | GGGTGAACCG | 11 | repulsion | 335 | *** | 1 | 1 | 1 | 1 | 1 | 1 | 1 |
| UBC-528 | GGATCTATGC | 12 | coupling | 528 | *** | 0 | 0 | 0 | 0 | 0 | 0 | 0 |
| UBC-534 | CACCCCCTGC | 13 | coupling | 436 | *** | 0 | 0 | 0 | 0 | 0 | 0 | 0 |
| UBC-544 | TAGAGACTCC | 14 | coupling | 499 | ** | 0 | 0 | 0 | 0 | 0 | 0 | 0 |
| UBC-563 | CGCCGCTCCT | 15 | coupling | 566 | ** | 0 | 0 | 0 | 0 | 0 | 0 | 0 |
| UBC-610 | TTTGCCGCCC | 16 | coupling | 528 | ** | 0 | 0 | 0 | 0 | 0 | 0 | 0 |
| UBC-624 | GTGATAAGCC | 17 | coupling | 480 | ** | 0 | 0 | 0 | 0 | 0 | 0 | 0 |

| PRIMER | LINES RESISTANT BULK | | | | | | |
|---|---|---|---|---|---|---|---|
| | Ovens 62 | DH 17 | DH 62 | NC-BMR-42 | NC-BMR-90 | NC-BMR-113 | NC-BMR-114 |
| OPAE-02 | 1 | 1 | 0 | 1 | 1 | 1 | 1 |
| OPAE-07 | 0 | 0 | 1 | 0 | 0 | 0 | 0 |
| OPAG-20 | 1 | 1 | 0 | 1 | 1 | 1 | 1 |
| OPC-09 | 1 | 1 | 0 | 1 | 1 | 1 | 1 |
| OPP-11 | 1 | 1 | 0 | 1 | 1 | 1 | 1 |
| OPR-06 | 1 | 1 | 0 | 1 | 1 | 1 | 1 |
| UBC-024 | 1 | 1 | 0 | 1 | 1 | 1 | 1 |
| UBC-149 | 1 | 1 | 0 | 1 | 1 | 1 | 1 |
| UBC-180 | 1 | 1 | 0 | 1 | 1 | 1 | 1 |
| UBC-240 | 0 | 0 | 1 | 0 | 0 | 0 | 0 |
| UBC-243 | 0 | 0 | 1 | 0 | 0 | 0 | 0 |
| UBC-528 | 1 | 1 | 0 | 1 | 1 | 1 | 1 |
| UBC-534 | 1 | 1 | 0 | 1 | 1 | 1 | 1 |
| UBC-544 | 1 | 1 | 0 | 1 | 1 | 1 | 1 |
| UBC-563 | 1 | 1 | 0 | 1 | 1 | 1 | 1 |
| UBC-610 | 1 | 1 | 0 | 1 | 1 | 1 | 1 |
| UBC-624 | 1 | 1 | 0 | 1 | 1 | 1 | 1 |

[a] * = fair,  = good, * = very good
[b] 0 = absence of the marker, 1 = presence of the marker

Having now described the invention, the same will be illustrated with reference to certain examples, which are included herein for illustration purposes only, and which are not intended to be limiting of the invention.

That which is claimed is:

1. A tobacco seed designated NC 2000, representative seed of said tobacco cultivar NC 2000 having been deposited under ATCC Accession No. PTA-3721.

2. A tobacco plant, or thereof, produced by the seed of claim 1.

3. Pollen of the plant of claim 2.

4. An ovule of the plant of claim 2.

5. A tobacco plant, or a part thereof, having all the physiological and morphological characteristics of tobacco cultivar NC 2000.

6. A tissue culture of regenerable cells of the plant of claim 2.

7. The tissue culture according to claim 6, the cells from a plant part selected from the group consisting of leaves, pollen, embryos, cotyledon, hypocotyl, roots, root tips, anthers, flowers and parts thereof, ovules, shoots, stems, stalks, pith and capsules or wherein the regenerable cells are callus or protoplasts derived therefrom.

8. A tobacco plant regenerated from the tissue culture of claim 6, wherein the plant expresses all the morphological and physiological characteristics of tobacco cultivar NC 2000.

9. A tobacco plant having all of the physiological and morphological characteristics of the tobacco plant of claim 2, said tobacco plant having been produced by a tissue culture process using the tobacco plant of claim 2 as the starting material.

10. A method for producing a first generation ($F_1$) hybrid tobacco seed wherein the method comprises crossing the plant of claim 2 with a different inbred or doubled-haploid parent tobacco plant and harvesting the resultant first generation ($F_1$) hybrid tobacco seed.

11. The method of claim 10, wherein the tobacco plant of claim 2 is a female parent.

12. The method of claim 10, wherein the tobacco plant of claim 2 is a male parent.

13. A method for producing a NC 2000-derived tobacco plant expressing resistance to blue mold caused by the fungal pathogen *Peronospora tabacina* Adam, wherein the method comprises:

(a) crossing tobacco cultivar NC 2000, representative seed of said tobacco cultivar NC 2000 having been deposited under ATCC Accession No. PTA-3721, with a second tobacco plant to yield progeny tobacco seed;

(b) growing said progeny tobacco seed, under plant growth coditions, to yield said NC 2000-derived tobacco plant expressing resistance to blue old caused by the fungal pathogen *Peronospora tabacina* Adam.

14. An herbicide-resistant tobacco plant, or a part thereof, produced by stably transforming the plant or part thereof of claim 8 with a transgene that confers herbicide resistance.

15. An herbicide-resistant tobacco plant, ro a part thereof, produced by stably transforming the plant or part thereof of claim 5 with transgene that confers herbicide resistance.

16. A disease-resistant tobacco plant, or a part thereof, produced by stably transforming the plant or part thereof of claim 8 with a transgene that confers disease resistance.

17. An insect-resistant tobacco plant, or a part thereof, produced by stably transforming the plant or part thereof of claim 8 with a transgene that confers insect resistance.

18. A disease-resistant tobacco plant, or a part thereof, produced by stably transforming the plant or part thereof of claim 5 with a trangene that confers disease resistant.

19. An insect-resistant tobacco plant, or a part thereof, produced by stably transforming the plant or part thereof of claim 5 with a transgene that confers insect resistance.

20. An herbicide-resistant tobacco plant, or a part thereof, produced by stably transforming the plant or part thereof of claim 2 with a transgene that confers herbicide resistance.

21. A disease-resistant tobacco plant, or a part thereof, produced by stably transforming the plant or part thereof of claim 2 with a transgene that confers disease resistance.

22. An insect-resistant tobacco plant, or a part thereof, produced by stably transforming the plant or part thereof of claim 2 with a transgene that confers insect resistance.

23. A method of making an herbicide-resistant tobacco plant wherein the method comprises stably transforming the plant of claim 2 with a transgene that confers herbicide resistance.

24. A method of making a disease-resistant tobacco plant wherein the method comprises stably transforming the plant of claim 2 with a transgene that confers disease resistance.

25. A method of making an insect-resistant tobacco plant wherein the method comprises stably transforming the plant of claim 2 with a transgene that confers insect resistance.

26. A method of making an herbicide-resistant tobacco plant wherein the method comprises stably transforming the plant of claim 5 with a transgene that confers herbicide resistance.

27. A method of making a disease-resistant tobacco plant wherein the method comprises stably transforming the plant of claim 5 with a transgene that confers disease resistance.

28. A method of making an insect-resistant tobacco plant wherein the method comprises stably transforming the plant of claim 5 with a transgene that onfers insect resistance.

29. A method of making an herbicide-resistant tobacco plant wherein the method comprises stably transforming the plant of claim 8 with a transgene that confers herbicide resistance.

30. A method of making a disease-resistant tobacco plant wherein the method comprises stably transforming the plant of claim 8 with a transgene that confers disease resistance.

31. A method of making an insect-resistant tobacco plant wherein the method comprises stably transforming the plant of claim 8 with a transgene that confers insect resistance.

32. A method of making a male sterile tobacco plant, wherein the method comprises crossing the tobacco plant of any one of claims 2, 5, 8 or 9 with a tobacco plant that has cytoplasmic male sterility.

33. The method of claim 10, wherein said different inbred or doubled-haploid parent tobacco plant has cytoplasmic male sterility.

34. The method of claim 13, wherein said second tobacco plant has cytoplasmic male sterility.

* * * * *

UNITED STATES PATENT AND TRADEMARK OFFICE
CERTIFICATE OF CORRECTION

PATENT NO.         : 6,965,062 B2
APPLICATION NO. : 10/247857
DATED                 : November 15, 2005
INVENTOR(S)       : Rufty It is certified that error appears in the above-identified patent and that said Letters Patent is hereby corrected as shown below:

In the Claims:

Column 35, line 31 should read:
-- 2. A tobacco plant, or a part thereof, produced by the seed of --

Column 36, line 32 should read:
--growth conditions, to yield said NC 2000-derived --

Column 36, line 33 should read:
-- tobacco plant expressing resistance to blue mold caused --

Column 36, line 38 should read:
-- 15. An herbicide-resistant tobacco plant, or a part thereof, --

Column 36, line 49 should read:
-- claim 5 with a transgene that confers disease resistance. --

Column 37, line 13 should read:
-- of claim 5 with a transgene that confers insect resistance. --

In columns 35-36, line 26, add
In the Appendix:

Pages 1, 2, 3, 4 as attached should be included as Appendix A.

Signed and Sealed this

Seventh Day of November, 2006

JON W. DUDAS
*Director of the United States Patent and Trademark Office*

FORM (Appendix A)

U.S. DEPARTMENT OF AGRICULTURE
AGRICULTURAL MARKETING SERVICE

OBJECTIVE DESCRIPTION OF VARIETY
Tobacco (Nicotiana tabacum)

| NAME OF APPLICANT(S) | EXPERIMENTAL DESIGNATION(S) | VARIETY NAME OR TEMPORARY DESIGNATION |
|---|---|---|
| North Carolina State University | DH 408 | NC 2000 |

| ADDRESS (Street and No. or R.F.D. No., City, State, and Zip Code) | FOR OFFICIAL USE ONLY |
|---|---|
| North Carolina State University, Office of the Vice Chancellor for Research and Graduate Studies, Campus Box 7003, Raleigh, North Carolina | PVPO NUMBER |

INSTRUCTIONS: Place the appropriate number that best describes the varietal character of typical plants in the blocks below. The symbol Δ indicates a decimal. Present data for Standard Varieties as requested.

STANDARD VARIETIES AND CODE NUMBERS

- 01 = NC 95
- 02 = NC 2326
- 03 = Coker 319
- 04 = Hicks
- 05 = Speight G-28
- 06 = SC 58
- 07 = McNair
- 08 = Burley 21
- 09 = KY 14
- 10 = KY 17
- 11 = VA 509
- 12 = Maryland 609
- 13 = KY 160
- 14 = Pennbel 69
- 15 = Havana 503
- 16 = Other

AREA OF ADAPTATION

1. CLASS [3]
- 1 = Flue-cured
- 2 = Fire-cured
- 3 = Burley
- 4 = Maryland
- 5 = Dark/air-cured
- 6 = Cigar filler
- 7 = Cigar binder
- 8 = Other

2. MATURITY (Transplant to 50% plants 1 fl.) (Select code from Standard Varieties listed above)

- [7][5] No. of days
- [ ][ ] No. of days earlier than ......... [ ][ ]
- Flowering same as ......... [ ][ ]
- [0][9] No. of days later than ......... [0][9]

Maturity Class: [3]
- 1 = Early (NC 2326, MS KY 14 X L8, MS Bu 37 X L8)
- 2 = Medium (NC 95, Speight G-28, Coker 319, KY 14, MS Bu 21 X KY 10)
- 3 = Late (NC 50, Coker 298, VA 509, R7-11)
- 4 = Very Late (NC 21NF, Bu 64)

3. PLANT HEIGHT (Select code from Standard Varieties listed above)

TOPPED NORMAL
- [1][0]Δ[8] cm tall
- [1][2] cm shorter than ......... [0][9]
- topped height same as ......... [ ][ ]
- [ ][ ] cm taller than ......... [ ][ ]

NOT TOPPED (Height to ground)
- [1][3][6] cm tall
- [1][3] cm shorter than ......... [0][9]
- non-topped height same as ......... [ ][ ]
- [ ][ ] cm taller than ......... [ ][ ]

Height Class:
- 1 = Short (Speight G-28, Bu 49, Bu 64)
- 2 = Medium (NC 95, NC 2326, Coker 319, KY 14, KY 17)
- 3 = Tall (Coker 48, Coker 298, C1 301, Bu 21, R7-11)

4. LEAF SIZE AND ANGLE (at leaf maturity of harvestable leaves counting from the bottom of plant) (Select code from Standard Varieties listed above):

LENGTH

5TH LEAF
- [5][9] cm length
- [1]Δ[3] cm shorter than ... [0][9]
- length same as .... [ ][ ]
- [ ][ ] cm longer than ... [ ][ ]

10TH LEAF
- [6][1][1] cm length
- [4][1] cm shorter than... [09]
- length same as ... [ ][ ]
- [ ][ ] cm longer than... [ ][ ]

15TH LEAF
- [5][6][7] cm length
- [8][5] cm shorter than... [0][9]
- length same as ... [ ][ ]
- [ ][ ] cm longer than... [ ][ ]

Leaf Length Class (10th leaf or center of plant): [2]
- 1 = Short (Bu 49, Bu 64)
- 2 = Medium (Bu 21, MS Bu 21 X KY 10)
- 3 = Long (MS Bu 21 X L4, R7-11)

FORM LS-470-31

4. LEAF SIZE AND ANGLE (cont'd)

WIDTH - 5TH LEAF
- [3][0][9] cm width
- [2][3] cm narrower than . [0][9]
- [ ][ ] width same as . . . [ ][ ]
- [ ][ ] cm wider than . . . [ ][ ]

WIDTH - 10TH LEAF
- [3][0][9] cm width
- [2][1] cm narrower than . [0][9]
- [ ][ ] width same as . . . [ ][ ]
- [ ][ ] cm wider than . . . [ ][ ]

WIDTH - 15TH LEAF
- [2][6][9] cm width
- [1][4] cm narrower than . [0][9]
- [ ][ ] width same as . . . [ ][ ]
- [ ][ ] cm wider than . . . [ ][ ]

[ ] Leaf Width Class (10th leaf or center of plant)
1 = Very Narrow
2 = Narrow (NC 2326, Bu 64, KY 10)
3 = Medium (Coker 319, MS Bu 21 X KY 10, KY 14)
4 = Broad (NC 13, Coker 139, MS Bu 21 X L8, CL 58)
5 = Very Broad

---

LEAF ANGLE (Upper angle between stalk and leaf when turgid)

5TH LEAF
- [4][8] degrees
- [ ][ ] degrees less than . [ ][ ]
- [ ][ ] angle same as . . . [ ][ ]
- [0][8] degrees more than . [ ][ ]

10TH LEAF
- [5][2] degrees
- [ ][ ] degrees less than . [ ][ ]
- [ ][ ] angle same as . . . [ ][ ]
- [0][8] degrees more than . [0][9]

15TH LEAF
- [5][5] degrees
- [ ][ ] degrees less than . [ ][ ]
- [ ][ ] angle same as . . . [0][9]
- [ ][ ] degrees more than . [ ][ ]

[3] Leaf Angle Class (10th leaf or center of plant)
1 = Upright ( 35 degrees) (Speight G-70, K 399, Bu 49, Bu 64)
2 = Medium Upright (35 - 45 degrees) (NC 72, Speight G-15, MD-10, KY 14, Bu 31)
3 = Medium Drooping (45 - 65 degrees) (Coker 48, Coker 176, MS KY 14 X L8)
4 = Drooping ( 65 degrees)

---

5. LEAF YIELD (Select code from Standard Varieties listed above)

- [2][9][4][6] kg/ha Yield
- [ ][ ] % less yield than . [ ][ ]
- [ ][ ] Yield same as . . . [1][1]
- [1][4] % more yield than . [0][9]

6. LEAF NUMBER (Not including 2 bad leaves) (Select code from Standard Varieties listed above)

TOPPED NORMAL
- [1][9] No. per plant
- [1][0] No. leaves less than . [0][9]
- [ ][ ] Leaf no. same as . . [ ][ ]
- [ ][ ][ ] No. leaves more than . [ ][ ]

NOT TOPPED (No. of leaves or nod to crowfoot from 1st harvestable lvs)
- [2][4] No. per plant
- [1][4] No. leaves less than . [0][9]
- [ ][ ] Leaf no. same as . . [ ][ ]
- [ ][ ][ ] No. leaves more than . [ ][ ]

---

7. INTERNODES AND STALKS (Plants topped normal) (Select code from Standard Varieties listed above)

- [6][2] mm length
- [2] mm shorter than . [0][9]
- [ ][ ] Internodes same as [ ][ ]
- [ ][ ] mm longer than . . [ ][ ]

[2] Internode Length Class
1 = Short (Speight G-28, Bu 64, Bu 49)
2 = Medium (Coker 319, KY 14)
3 = Long (NC 2326, MS Bu 21 X L8)

[2] Stalk Diameter Class
1 = Small (KY 14, MS Bu 21 X KY 10)
2 = Medium (MS KY 14 X L8, E7-11)
3 = Large (VA 509, KY 17)

8. LEAF CHARACTERISTICS

[2] LEAF CARRIAGE (Midrib)
1 = Arched
2 = Not arched (Coker 347, Bu 21)

[1] TIP SHAPE
1 = Acute (MD 64)
2 = Acuminate (Speight G-70, McNair 373, Coker 48)
3 = Obtuse (MD 872, Reams 64, NC 15)

[2] LEAF MARGIN
1 = Wavy (McNair 944, MD 59)
2 = Not wavy (McNair 373, Speight G-70)

[1] LEAF COLOR
1 = Light green (Coker 298, K 399, MD 609)
2 = Green (NC 95, Coker 48)
3 = Dark green (MD 10, MD 201, KY 14, KY 15)

[1] VENATION PATTERN
1 = Square (McNair 944)
2 = Angular (Speight G-70, Hicks)

[1] LEAF MARGIN CURVING
1 = Recurved (MD 59)
2 = Not recurved (Speight G-70, McNair 373)

[2] LEAF SHAPE
1 = Broadest at middle of leaf (Coker 178)
2 = Broadest below middle (K 399, McNair 373)
3 = Broadest above middle (Speight G-140)

[2] LEAF SURFACE (Web, Rugosity)
1 = Smooth (Hicks, Speight G-70)
2 = Puckered (NC 95)

9. FLOWERS

[2] COLOR
1 = White
2 = Pink
3 = Red
4 = Other (Specify) _____

[1] FLOWER HEAD HABIT
1 = Closed (NC 95, Bu 21)
2 = Intermediate (NC 55)
3 = Open (Hicks, NC 2326)

10. PLANT FORM

[1]
1 = Pyramidal (Coker 176)
2 = Columnar (K 326, Bu 49, Bu 64)
3 = Inverted cone
4 = Other

11. GROUND SUCKERS (Select code from Standard Varieties)

[0][3] No. per plant
[ ][2] No. per plant less than [0][9]
[ ][ ] No. per plant same as ___
[ ][ ] No. per plant more than ___

12. DISEASE

0 = Not tested
1 = Susceptible
2 = Low resistance
3 = Moderate resistance
4 = High resistance

[1] Black Shank (Phytophthora parasitica var. nicotianae race 0)
[1] Black Shank (Phytophthora parasitica var. nicotianae race 1)
[1] Black Root Rot (Thielaviopsis basicola)
[3] Blue Mold (Peronospora tabacina)
[4] Wildfire (Pseudomonas tabaci)
[1] Blackfire or Angular Leaf Spot (Pseudomonas angulata)
[1] Fusarium Wilt (F. oxysporum var. nicotianae)
[1] Fusarium Wilt (F. oxysporum var. batatas)
[1] Frogeye (Cercospora nicotianae)
[1] Brown Spot (Alternaria alternata)

[1] Bacterial Wilt (Granville Wilt) (Pseudomonas solanacearum)
[1] Potato Virus Y (Vein banding)
[1] Tobacco Vein Mottling Virus (TVMV)
[4] Tobacco Mosaic Virus (TMV)
[1] Tobacco Etch Virus
[1] Cyst Nematode (Heterodera tabacum)
[1] Nematode Root Rot (Lesion) (Pratylenchus spp.) Species _____
[1] Root Knot Nematode (Meloidogyne spp.) Species _____
[0] Ozone Air Pollution (Weather fleck)
[ ] Other (Specify) _____
[ ] Other (Specify) _____

13. LEAF CONSTITUENTS (Give data for application and a Standard Variety)

[4][9][5] % Nicotine
[0][5][0] % Nor Nicotine
[4][5][6] % Total Nitrogen
[ ][ ][ ] % R. Sugars Flue-cured

[4][1][0] % Nicotine (standard) KY 14
[0][4][2] % Nor Nicotine (standard) KY 14
[4][6][0] % Total Nitrogen (standard) KY 14
[ ][ ][ ] % R. Sugars Flue-cured (standard) _____

14. GIVE VARIETY OR VARIETIES THAT MOST CLOSELY RESEMBLE(S) THE APPLICATION VARIETY. (For the following characteristics a "Degree of Resemblance" by placing in the column marked "D.R." one of the following numbers)

1 = Application variety is less than comparison variety
   2 = Same as
   3 = More than, better, greater, darker, etc.

| CHARACTERISTICS | VARIETY(S) | D.R. | CHARACTERISTICS | VARIETY(S) | D.R. |
|---|---|---|---|---|---|
| Flowering | | | Leaf tip shape | | |
| Leaf length | | | Venation pattern | | |
| Leaf width | | | Leaf surface | | |
| Leaf carriage | | | Leaf margin | | |
| Petiole angle | | | Leaf color | | |
| Leaf shade | | | Plant form | | |

15. COMMENTS (Describe all characters and conditions that cannot be adequately described in this form (lodging resistance, disease ratings, comparison standard checks, etc.)

UNITED STATES PATENT AND TRADEMARK OFFICE
CERTIFICATE OF CORRECTION

| | |
|---|---|
| PATENT NO. | : 6,965,062 B2 |
| APPLICATION NO. | : 10/247857 |
| DATED | : November 15, 2005 |
| INVENTOR(S) | : Rufty |

It is certified that error appears in the above-identified patent and that said Letters Patent is hereby corrected as shown below:

In the Claims:

Column 35, line 31 should read:
-- 2. A tobacco plant, or a part thereof, produced by the seed of --

Column 36, line 32 should read:
--growth conditions, to yield said NC 2000-derived --

Column 36, line 33 should read:
-- tobacco plant expressing resistance to blue mold caused --

Column 36, line 38 should read:
-- 15. An herbicide-resistance tobacco plant, or a part thereof, --

Column 36, line 49 should read:
-- claim 5 with a transgene that confers disease resistance. --

Column 37, line 13 should read:
-- of claim 5 with a transgene that confers insect resistance. --

In columns 35-36, line 26, add
In the Appendix:

Pages 1, 2, 3, 4 as attached should be included as Appendix A.

This certificate supersedes Certificate of Correction issued November 7, 2006.

Signed and Sealed this

Twentieth Day of February, 2007

JON W. DUDAS
*Director of the United States Patent and Trademark Office*

FORM (APPENDIX A) 1581-01

U.S. DEPARTMENT OF AGRICULTURE
AGRICULTURAL MARKETING SERVICE

OBJECTIVE DESCRIPTION OF VARIETY
Tobacco (Nicotiana tabacum)

| NAME OF APPLICANT(S) | EXPERIMENTAL DESIGNATION(S) | VARIETY NAME OR TEMPORARY DESIGNATION |
|---|---|---|
| North Carolina State University | DH 408 | NC 2000 |

| ADDRESS (Street and No. or R.F.D. No., City, State, and Zip Code) | FOR OFFICIAL USE ONLY |
|---|---|
| North Carolina State University, Office of the Vice Chancellor for Research and Graduate Studies, Campus Box 7003, Raleigh, North Carolina | PVPO NUMBER |

INSTRUCTIONS: Place the appropriate number that best describes the varietal character of typical plants in the blocks below. The symbol △ indicates a decimal. Present data for Standard Varieties as requested.

STANDARD VARIETIES AND CODE NUMBERS

01 = NC 95        04 = Hicks          07 = Madole       10 = KY 17       13 = KY 160
02 = NC 2326      05 = Speight G-28   08 = Burley 21    11 = VA 509      14 = Pennbel 69
03 = Coker 319    06 = SC 58          09 = KY 14        12 = Maryland 609 15 = Havana 503
                                                                          16 = Other

AREA OF ADAPTATION

1. CLASS  [3]
1 = Flue-cured    3 = Burley        5 = Dark/air-cured   7 = Cigar binder
2 = Fire-cured    4 = Maryland      6 = Cigar filler     8 = Other

2. MATURITY (Transplant to 50% plants 1 fl.) (Select code from Standard Varieties listed above)

[7][5] No. of days

[ ][ ] No. of days earlier than ........ [ ][ ]

Flowering same as ........ [ ][ ]

[0][9] No. of days later than ........ [0][9]

Maturity Class:
1 = Early (NC 2326, MS KY 14 X L8, MS Bu 37 X L8)
[3] 2 = Medium (NC 95, Speight G-28, Coker 319, KY 14, MS Bu 21 X KY 10)
3 = Late (NC 50, Coker 298, VA 509, R7-11)
4 = Very Late (NC 21NF, Bu 64)

3. PLANT HEIGHT (Select code from Standard Varieties listed above)

TOPPED NORMAL

[1][0]△[8] cm tall

[1][2] cm shorter than ........ [0][9]

topped height same as ........ [ ][ ]

[ ][ ] cm taller than ........ [ ][ ]

NOT TOPPED (Height to ground)

[1][3][6] cm tall

[1][3] cm shorter than ........ [0][9]

non-topped height same as ........ [ ][ ]

[ ][ ] cm taller than ........ [ ][ ]

Height Class:
[ ] 1 = Short (Speight G-28, Bu 49, Bu 64)
2 = Medium (NC 95, NC 2326, Coker 319, KY 14, KY 17)
3 = Tall (Coker 48, Coker 298, C1 301, Bu 21, R7-11)

4. LEAF SIZE AND ANGLE (at leaf maturity of harvestable leaves counting from the bottom of plant) (Select code from Standard Varieties listed above):

LENGTH

5TH LEAF
[5][9] cm length
[1][?][3] cm shorter than ... [0][9]
length same as .... [ ][ ]
cm longer than .... [ ][ ]

10TH LEAF
[6][1][1] cm length
[4][1] cm shorter than ... [0][9]
length same as .... [ ][ ]
cm longer than .... [ ][ ]

15TH LEAF
[5][6][7] cm length
[8][5] cm shorter than ... [0][9]
length same as .... [ ][ ]
cm longer than .... [ ][ ]

Leaf Length Class (10th leaf or center of plant):
[2] 1 = Short (Bu 49, Bu 64)
2 = Medium (Bu 21, MS Bu 21 X KY 10)
3 = Long (MS Bu 21 X L4, R7-11)

FORM LS-470-31 ___ Form LPGS-470-31, which is obsolete.

4. LEAF SIZE AND ANGLE (cont'd)

WIDTH - 5TH LEAF
- [3][0][9] cm width
- [2][3] cm narrower than . [0][9]
- [ ][ ] width same as . . . [ ][ ]
- [ ][ ] cm wider than . . . [ ][ ]

WIDTH - 10TH LEAF
- [3][0][9] cm width
- [2][1] cm narrower than . [0][9]
- [ ][ ] width same as . . . [ ][ ]
- [ ][ ] cm wider than . . . [ ][ ]

WIDTH - 15TH LEAF
- [2][6][9] cm width
- [1][4] cm narrower than . [0][9]
- [ ][ ] width same as . . . [ ][ ]
- [ ][ ] cm wider than . . . [ ][ ]

[ ] Leaf Width Class (10th leaf or center of plant)
1 = Very Narrow
2 = Narrow (NC 2326, Bu 64, KY 10)
3 = Medium (Coker 319, MS Bu 21 X KY 10, KY 14)
4 = Broad (NC 12, Coker 139, MS Bu 21 X L8, CL 58)
5 = Very Broad

LEAF ANGLE (Upper angle between stalk and leaf when turgid)

5TH LEAF
- [4][8] degrees
- [ ][ ] degrees less than . . [ ][ ]
- [ ][ ] angle same as . . . [ ][ ]
- [0][8] degrees more than . [ ][ ]

10TH LEAF
- [5][2] degrees
- [ ][ ] degrees less than . . [ ][ ]
- [ ][ ] angle same as . . . [ ][ ]
- [0][8] degrees more than . [0][9]

15TH LEAF
- [5][5] degrees
- [ ][ ] degrees less than . . [ ][ ]
- [ ][ ] angle same as . . . [0][9]
- [ ][ ] degrees more than . [ ][ ]

[3] Leaf Angle Class (10th leaf or center of plant)
1 = Upright ( 35 degrees) (Speight G-70, K 399, Bu 49, Bu 64)
2 = Medium Upright (35 - 45 degrees) (NC 72, Speight G-15, MD-10, KY 14, Bu 31)
3 = Medium Drooping (46 - 65 degrees) (Coker 48, Coker 176, MS KY 14 X L8)
4 = Drooping ( 65 degrees)

5. LEAF YIELD (Select code from Standard Varieties listed above)
- [2][9][4][6] kg/ha Yield
- [ ][ ] % less yield than . [ ][ ]
- [ ][ ] Yield same as . . . [1][1]
- [1][4] % more yield than . [0][9]

6. LEAF NUMBER (Not including 2 bad leaves) (Select code from Standard Varieties listed above)

TOPPED NORMAL
- [1][9] No. per plant
- [1][0] No. leaves less than . [0][9]
- [ ][ ] Leaf no. same as . . [ ][ ]
- [ ][ ] No. leaves more than [ ][ ]

NOT TOPPED (No. of leaves or nod to crowfoot from 1st harvestable lvs)
- [2][4] No. per plant
- [1][4] No. leaves less than . [0][9]
- [ ][ ] Leaf no. same as . . [ ][ ]
- [ ][ ] No. leaves more than [ ][ ]

7. INTERNODES AND STALKS (Plants topped normal) (Select code from Standard Varieties listed above)

- [6][2] mm length
- [2] mm shorter than . [0][9]
- [ ][ ] internodes same as [ ][ ]
- [ ][ ] mm longer than . . [ ][ ]

[2] Internode Length Class
1 = Short (Speight G-28, Bu 64, Bu 49)
2 = Medium (Coker 319, KY 14)
3 = Long (NC 2326, MS Bu 21 X L8)

[2] Stalk Diameter Class
1 = Small (KY 14, MS Bu 21 X KY 10)
2 = Medium (MS KY 14 X L8, E7-11)
3 = Large (VA 509, KY 17)

8. LEAF CHARACTERISTICS

[2] LEAF CARRIAGE (Midrib)
1 = Arched
2 = Not arched (Coker 347, Bu 21)

[1] TIP SHAPE
1 = Acute (MD 64)
2 = Acuminate (Speight G-70, McNair 373, Coker 48)
3 = Obtuse (MD 872, Reams 64, NC 15)

[2] LEAF MARGIN
1 = Wavy (McNair 944, MD 59)
2 = Not wavy (McNair 373, Speight G-70)

[1] LEAF COLOR
1 = Light green (Coker 298, K 399, MD 609)
2 = Green (NC 95, Coker 48)
3 = Dark green (MD 10, MD 201, KY 14, KY 15)

[1] VENATION PATTERN
1 = Square (McNair 944)
2 = Angular (Speight G-70, Hicks)

[1] LEAF MARGIN CURVING
1 = Recurved (MD 59)
2 = Not recurved (Speight G-70, McNair 373)

[2] LEAF SHAPE
1 = Broadest at middle of leaf (Coker 178)
2 = Broadest below middle (K 399, McNair 373)
3 = Broadest above middle (Speight G-140)

[2] LEAF SURFACE (Web, Rugosity)
1 = Smooth (Hicks, Speight G-70)
2 = Puckered (NC 95)

9. FLOWERS

[2] COLOR
1 = White
2 = Pink
3 = Red
4 = Other (Specify) _____

[1] FLOWER HEAD HABIT
1 = Closed (NC 95, Bu 21)
2 = Intermediate (NC 88)
3 = Open (Hicks, NC 2326)

10. PLANT FORM

[1]
1 = Pyramidal (Coker 176)
2 = Columnar (K 326, Bu 49, Bu 64)
3 = Inverted cone
4 = Other

11. GROUND SUCKERS (Select code from Standard Varieties)

[0][3] No. per plant
[ ][2] No. per plant less than [0][9]
[ ][ ] No. per plant same as [ ][ ]
[ ][ ] No. per plant more than [ ][ ]

12. DISEASE

0 = Not rated   2 = Low resistance   4 = High resistance
1 = Susceptible   3 = Moderate resistance

[1] Black Shank (Phytophthora parasitica var. nicotianae race 0)
[1] Black Shank (Phytophthora parasitica var. nicotianae race 1)
[1] Black Root Rot (Thielaviopsis basicola)
[3] Blue Mold (Peronospora tabacina)
[4] Wildfire (Pseudomonas tabaci)
[1] Blackfire or Angular Leaf Spot (Pseudomonas angulata)
[1] Fusarium Wilt (F. oxysporum var. nicotianae)
[1] Fusarium Wilt (F. oxysporum var. batatas)
[1] Frogeye (Cercospora nicotianae)
[1] Brown Spot (Alternaria alternata)

[1] Bacterial Wilt (Granville Wilt) (Pseudomonas solanacearum)
[1] Potato Virus Y (Vein banding)
[1] Tobacco Vein Mottling Virus (TVMV)
[4] Tobacco Mosaic Virus (TMV)
[1] Tobacco Etch Virus
[1] Cyst Nematode (Heterodera tabacum)
[1] Nematode Root Rot (Lesion) (Pratylenchus spp.) Species _____
[1] Root Knot Nematode (Meloidogyne spp.) Species _____
[0] Ozone Air Pollution (Weather fleck)
[ ] Other (Specify) _____
[ ] Other (Specify) _____

13. LEAF CONSTITUENTS (Give data for application and a Standard Variety)

[4][9][5] % Nicotine           [4][1][0] % Nicotine (standard) KY 14
[0][5][0] % Nor Nicotine       [0][4][2] % Nor Nicotine (standard) KY 14
[4][5][6] % Total Nitrogen     [4][6][0] % Total Nitrogen (standard) KY 14
[ ][ ][ ] % R. Sugars Flue-cured   [ ][ ][ ] % R. Sugars Flue-cured (standard) _____

14. GIVE VARIETY OR VARIETIES THAT MOST CLOSELY RESEMBLE(S) THE APPLICATION VARIETY. (For the following characteristics it "Degree of Resemblance" by placing in the column marked "D.R." one of the following numbers)

1 = Application variety is less than comparison variety
2 = Same as
3 = More than, better, greater, darker, etc.

| CHARACTERISTICS | VARIETY(S) | D.R. | CHARACTERISTICS | VARIETY(S) | D.R. |
|---|---|---|---|---|---|
| Flowering | | | Leaf tip shape | | |
| Leaf length | | | Venation pattern | | |
| Leaf width | | | Leaf surface | | |
| Leaf carriage | | | Leaf margin | | |
| Petiole angle | | | Leaf color | | |
| Leaf shape | | | Plant form | | |

15. COMMENTS (Describe all characters and conditions that cannot be adequately described in this form (lodging resistance disease ratings compare standard checks, etc.)